US011857314B2

United States Patent
Booth et al.

(10) Patent No.: US 11,857,314 B2
(45) Date of Patent: Jan. 2, 2024

(54) INSULIN MANAGEMENT

(71) Applicant: Aseko, Inc., Greenville, SC (US)

(72) Inventors: Robert C. Booth, Columbus, NC (US); Harry Hebblewhite, Atlanta, GA (US)

(73) Assignee: Aseko, Inc., Greenville, SC (US)

( * ) Notice: Subject to any disclaimer, the term of this patent is extended or adjusted under 35 U.S.C. 154(b) by 0 days.

(21) Appl. No.: 18/050,591

(22) Filed: Oct. 28, 2022

(65) Prior Publication Data

US 2023/0087860 A1    Mar. 23, 2023

Related U.S. Application Data

(63) Continuation of application No. 17/659,652, filed on Apr. 18, 2022, now Pat. No. 11,490,837, which is a
(Continued)

(51) Int. Cl.
*A61B 5/145* (2006.01)
*A61M 5/172* (2006.01)
(Continued)

(52) U.S. Cl.
CPC ........ *A61B 5/14532* (2013.01); *A61B 5/4839* (2013.01); *A61M 5/1723* (2013.01);
(Continued)

(58) Field of Classification Search
CPC ........ G16H 20/17; G16H 50/50; G16H 50/30; G16H 20/10; A61B 5/14532; A61B 5/0002; A61M 2230/201; A61M 5/1723
See application file for complete search history.

(56) References Cited

U.S. PATENT DOCUMENTS 561,422 A    6/1896   Minnis
4,055,175 A  10/1977  Clemens et al.
(Continued)

FOREIGN PATENT DOCUMENTS

AU    199460325 A    8/1994
AU    2009283013 A1  2/2010
(Continued)

OTHER PUBLICATIONS

Kim, Sarah et al., Hyperglycemia control of the Nil per os patient in the intensive care unit: Introduction of a simple subcutaneous insulin algorithm, Journal of Diabetes Science and Technology, Nov. 2012, vol. 6, Issue 6, pp. 1413-1419.
(Continued)

*Primary Examiner* — Scott J Medway
(74) *Attorney, Agent, or Firm* — Honigman LLP; Brett A. Krueger; Grant J. Griffith

(57) ABSTRACT

A method of managing insulin includes receiving blood glucose measurements on a computing device from a glucometer. The blood glucose measurements are separated by a time interval. The method includes determining, by the computing device, an insulin dose rate based on the blood glucose measurements and determining a blood glucose drop rate based on the blood glucose measurements and the time interval. The method also includes determining a blood glucose percentage drop based on the blood glucose measurements. The method includes decreasing the time interval between blood glucose measurements by the glucometer when the blood glucose drop rate is greater than a threshold drop rate, and decreasing the time interval between blood glucose measurements by the glucometer when the blood glucose percentage drop is greater than a threshold percentage drop.

20 Claims, 20 Drawing Sheets

Related U.S. Application Data continuation of application No. 15/856,363, filed on Dec. 28, 2017, now Pat. No. 11,311,213, which is a continuation of application No. 15/623,065, filed on Jun. 14, 2017, now Pat. No. 9,892,235, which is a continuation of application No. 15/342,102, filed on Nov. 2, 2016, now Pat. No. 9,710,611, which is a continuation of application No. 14/511,060, filed on Oct. 9, 2014, now Pat. No. 9,486,580.

(60) Provisional application No. 61/934,300, filed on Jan. 31, 2014.

(51) Int. Cl.
*G16H 40/63* (2018.01)
*G16H 40/67* (2018.01)
*A61B 5/00* (2006.01)
*G16H 20/17* (2018.01)
*G16H 10/00* (2018.01)
*A61M 5/142* (2006.01)

(52) U.S. Cl.
CPC ............ *G16H 10/00* (2018.01); *G16H 20/17* (2018.01); *G16H 40/63* (2018.01); *G16H 40/67* (2018.01); *A61B 5/7275* (2013.01); *A61M 2005/14296* (2013.01); *A61M 2205/18* (2013.01); *A61M 2205/3553* (2013.01); *A61M 2205/3561* (2013.01); *A61M 2205/3569* (2013.01); *A61M 2205/50* (2013.01); *A61M 2205/502* (2013.01); *A61M 2205/52* (2013.01); *A61M 2230/201* (2013.01)

(56) References Cited

U.S. PATENT DOCUMENTS

| | | | |
|---|---|---|---|
| 4,151,845 A | 5/1979 | Clemens | |
| 4,206,755 A | 6/1980 | Klein | |
| 4,403,984 A | 9/1983 | Ash et al. | |
| 4,464,170 A | 8/1984 | Clemens et al. | |
| 4,731,726 A | 3/1988 | Allen, III | |
| 4,850,959 A | 7/1989 | Findl | |
| 4,911,168 A | 3/1990 | Davis | |
| 4,947,845 A | 8/1990 | Davis | |
| 4,981,779 A | 1/1991 | Wagner | |
| 5,091,190 A | 2/1992 | Kuczynski et al. | |
| 5,216,597 A | 6/1993 | Beckers | |
| 5,251,126 A | 10/1993 | Kahn et al. | |
| 5,614,224 A | 3/1997 | Womack | |
| 5,665,065 A * | 9/1997 | Colman | A61M 5/1723 604/67 |
| 5,822,715 A | 10/1998 | Worthington et al. | |
| 5,956,501 A | 9/1999 | Brown | |
| 5,998,363 A | 12/1999 | Forse et al. | |
| 6,024,699 A | 2/2000 | Surwit et al. | |
| 6,186,145 B1 | 2/2001 | Brown | |
| 6,233,539 B1 | 5/2001 | Brown | |
| 6,379,301 B1 | 4/2002 | Worthington et al. | |
| 6,428,825 B2 | 8/2002 | Sharma et al. | |
| 6,472,366 B2 | 10/2002 | Kishino et al. | |
| 6,540,672 B1 | 4/2003 | Simonsen et al. | |
| 6,544,212 B2 | 4/2003 | Galley et al. | |
| 6,551,276 B1 * | 4/2003 | Mann | A61M 5/172 604/131 |
| 6,560,471 B1 | 5/2003 | Heller et al. | |
| 6,572,542 B1 | 6/2003 | Houben et al. | |
| 6,575,905 B2 | 6/2003 | Knobbe et al. | |
| 6,605,039 B2 | 8/2003 | Houben et al. | |
| 6,615,081 B1 | 9/2003 | Boveja | |
| 6,669,663 B1 | 12/2003 | Thompson | |
| 6,740,072 B2 | 5/2004 | Starkweather et al. | |
| 6,808,703 B2 | 10/2004 | Park et al. | |
| 6,890,568 B2 | 5/2005 | Pierce et al. | |
| 6,925,393 B1 * | 8/2005 | Kalatz | G16H 20/17 702/22 |
| 6,927,246 B2 | 8/2005 | Noronha et al. | |
| 7,025,425 B2 | 4/2006 | Kovatchev et al. | |
| 7,039,560 B2 | 5/2006 | Kawatahara et al. | |
| 7,060,059 B2 | 6/2006 | Keith et al. | |
| 7,108,680 B2 | 9/2006 | Rohr et al. | |
| 7,137,951 B2 | 11/2006 | Pilarski | |
| 7,167,818 B2 | 1/2007 | Brown | |
| 7,204,823 B2 | 4/2007 | Estes et al. | |
| 7,267,665 B2 | 9/2007 | Steil et al. | |
| 7,282,029 B1 | 10/2007 | Poulsen et al. | |
| 7,291,107 B2 | 11/2007 | Hellwig et al. | |
| 7,404,796 B2 | 7/2008 | Ginsberg | |
| 7,498,318 B1 | 3/2009 | Stahl et al. | |
| 7,509,156 B2 | 3/2009 | Flanders | |
| 7,553,281 B2 | 6/2009 | Hellwig et al. | |
| 7,651,845 B2 | 1/2010 | Doyle, III et al. | |
| 7,704,226 B2 | 4/2010 | Mueller, Jr. et al. | |
| 7,734,323 B2 | 6/2010 | Blomquist et al. | |
| 7,806,886 B2 | 10/2010 | Kanderian, Jr. et al. | |
| 7,824,333 B2 | 11/2010 | Otto et al. | |
| 7,837,622 B2 | 11/2010 | Itoh et al. | |
| 7,853,455 B2 | 12/2010 | Brown | |
| 7,877,271 B2 | 1/2011 | Brown | |
| 7,901,625 B2 | 3/2011 | Brown | |
| 7,904,310 B2 | 3/2011 | Brown | |
| 7,912,688 B2 | 3/2011 | Brown | |
| 7,920,998 B2 | 4/2011 | Brown | |
| 7,949,507 B2 | 5/2011 | Brown | |
| 7,976,778 B2 * | 7/2011 | Drucker | A61B 5/742 422/68.1 |
| 7,985,848 B2 | 7/2011 | Woo et al. | |
| 8,088,731 B2 | 1/2012 | Knudsen et al. | |
| 8,117,020 B2 | 2/2012 | Abensour et al. | |
| 8,185,412 B1 | 5/2012 | Harpale | |
| 8,198,320 B2 | 6/2012 | Liang et al. | |
| 8,204,729 B2 | 6/2012 | Sher | |
| 8,206,340 B2 | 6/2012 | Arefieg | |
| 8,257,300 B2 | 9/2012 | Budiman et al. | |
| 8,257,735 B2 | 9/2012 | Lau et al. | |
| 8,318,221 B2 | 11/2012 | Miller et al. | |
| 8,329,232 B2 | 12/2012 | Cheng et al. | |
| 8,333,752 B2 | 12/2012 | Veit et al. | |
| 8,370,077 B2 | 2/2013 | Bashan et al. | |
| 8,398,616 B2 | 3/2013 | Budiman | |
| 8,420,125 B2 | 4/2013 | Webster et al. | |
| 8,420,621 B2 | 4/2013 | Lai et al. | |
| 8,457,901 B2 | 6/2013 | Beshan et al. | |
| 8,527,208 B2 | 9/2013 | Prud'homme et al. | |
| 8,532,933 B2 | 9/2013 | Duke et al. | |
| 8,548,544 B2 | 10/2013 | Kircher, Jr. et al. | |
| 8,571,801 B2 | 10/2013 | Anfinsen et al. | |
| 8,579,879 B2 | 11/2013 | Palerm et al. | |
| 8,600,682 B2 | 12/2013 | Bashan et al. | |
| 8,635,054 B2 | 1/2014 | Brown | |
| 8,679,016 B2 | 3/2014 | Mastrototaro et al. | |
| 8,690,934 B2 | 4/2014 | Boyden et al. | |
| 8,700,161 B2 | 4/2014 | Harel et al. | |
| 8,703,183 B2 | 4/2014 | Lara | |
| 8,718,949 B2 | 5/2014 | Blomquist et al. | |
| 8,755,938 B2 | 6/2014 | Weinert et al. | |
| 8,766,803 B2 | 7/2014 | Bousamra et al. | |
| 8,771,251 B2 * | 7/2014 | Ruchti | G16H 20/17 604/67 |
| 8,828,390 B2 | 9/2014 | Herrera et al. | |
| 8,834,367 B2 | 9/2014 | Laan et al. | |
| 8,870,807 B2 | 10/2014 | Mantri et al. | |
| 8,911,367 B2 | 12/2014 | Brister et al. | |
| 8,919,180 B2 | 12/2014 | Gottlieb et al. | |
| 8,992,464 B2 | 3/2015 | Bashan et al. | |
| 9,446,194 B2 | 9/2016 | Kamath | |
| 9,872,890 B2 * | 1/2018 | Davidson | A61M 5/20 |
| 9,878,097 B2 * | 1/2018 | Estes | G16H 20/17 |
| 2001/0002269 A1 | 5/2001 | Zhao | |
| 2003/0028089 A1 | 2/2003 | Galley et al. | |
| 2003/0050621 A1 | 3/2003 | Lebel et al. | |
| 2003/0055570 A1 * | 3/2003 | Ribeiro, Jr. | G16H 40/60 702/19 |

(56) References Cited

U.S. PATENT DOCUMENTS

| | | |
|---|---|---|
| 2003/0199445 A1 | 10/2003 | Knudsen et al. |
| 2003/0208110 A1 | 11/2003 | Mault et al. |
| 2004/0042272 A1 | 3/2004 | Kurata |
| 2004/0044272 A1 | 3/2004 | Moerman et al. |
| 2004/0054263 A1 | 3/2004 | Moerman et al. |
| 2005/0020681 A1 | 1/2005 | Takayama et al. |
| 2005/0049179 A1 | 3/2005 | Davidson et al. |
| 2005/0054818 A1 | 3/2005 | Brader et al. |
| 2005/0055010 A1 | 3/2005 | Pettis et al. |
| 2005/0096637 A1 | 5/2005 | Heruth |
| 2005/0171503 A1 | 8/2005 | Van Den Berghe et al. |
| 2005/0176621 A1 | 8/2005 | Brader et al. |
| 2005/0177398 A1 | 8/2005 | Watanabe et al. |
| 2005/0187749 A1 | 8/2005 | Singley |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0267195 A1 | 12/2005 | Mikoshiba et al. |
| 2005/0272640 A1 | 12/2005 | Doyle et al. |
| 2006/0040003 A1 | 2/2006 | Needleman et al. |
| 2006/0078593 A1 | 4/2006 | Strozier et al. |
| 2006/0160722 A1 | 7/2006 | Green et al. |
| 2006/0173260 A1 | 8/2006 | Gaoni et al. |
| 2006/0188995 A1 | 8/2006 | Ryan et al. |
| 2006/0224109 A1 | 10/2006 | Steil et al. |
| 2006/0264895 A1 | 11/2006 | Flanders |
| 2007/0036872 A1 | 2/2007 | Tsuboi et al. |
| 2007/0060796 A1 | 3/2007 | Kim |
| 2007/0078314 A1 | 4/2007 | Grounsell et al. |
| 2007/0078818 A1 | 4/2007 | Zivitz et al. |
| 2007/0160678 A1 | 7/2007 | Guimberteau et al. |
| 2007/0168224 A1 | 7/2007 | Letzt et al. |
| 2007/0249916 A1 | 10/2007 | Pesach et al. |
| 2007/0282186 A1 | 12/2007 | Gilmore |
| 2007/0293742 A1 | 12/2007 | Simonsen et al. |
| 2008/0097289 A1 | 4/2008 | Steil et al. |
| 2008/0119421 A1 | 5/2008 | Tuszynski et al. |
| 2008/0119705 A1 | 5/2008 | Patel et al. |
| 2008/0139511 A1 | 6/2008 | Friesen |
| 2008/0139907 A1 | 6/2008 | Rao et al. |
| 2008/0172027 A1 * | 7/2008 | Blomquist ............. G16H 20/17 604/500 |
| 2008/0172030 A1 | 7/2008 | Blomquist |
| 2008/0188796 A1 | 8/2008 | Steil et al. |
| 2008/0214919 A1 | 9/2008 | Harmon et al. |
| 2008/0228056 A1 | 9/2008 | Blomquist et al. |
| 2008/0234943 A1 | 9/2008 | Ray et al. |
| 2008/0255707 A1 | 10/2008 | Hebblewhite et al. |
| 2008/0269585 A1 | 10/2008 | Ginsberg |
| 2008/0299079 A1 | 12/2008 | Meezan et al. |
| 2008/0306353 A1 | 12/2008 | Douglas et al. |
| 2009/0029933 A1 | 1/2009 | Velloso et al. |
| 2009/0036753 A1 | 2/2009 | King |
| 2009/0054753 A1 | 2/2009 | Robinson et al. |
| 2009/0069636 A1 | 3/2009 | Zivitz et al. |
| 2009/0099438 A1 | 4/2009 | Flanders |
| 2009/0110752 A1 | 4/2009 | Shang et al. |
| 2009/0149717 A1 * | 6/2009 | Brauer .................. G16H 20/60 600/300 |
| 2009/0214511 A1 | 8/2009 | Tran et al. |
| 2009/0227514 A1 | 9/2009 | Oben |
| 2009/0239944 A1 | 9/2009 | D'orazio et al. |
| 2009/0240127 A1 | 9/2009 | Ray |
| 2009/0242399 A1 | 10/2009 | Kamath et al. |
| 2009/0247982 A1 | 10/2009 | Krulevitch et al. |
| 2009/0253970 A1 | 10/2009 | Bashan et al. |
| 2009/0253973 A1 | 10/2009 | Bashan et al. |
| 2009/0281519 A1 | 11/2009 | Rao et al. |
| 2009/0299152 A1 | 12/2009 | Taub et al. |
| 2009/0312250 A1 | 12/2009 | Ryu et al. |
| 2010/0016700 A1 | 1/2010 | Sieh et al. |
| 2010/0035795 A1 | 2/2010 | Boss et al. |
| 2010/0125241 A1 * | 5/2010 | Prud'homme ......... G16H 20/17 600/300 |
| 2010/0137788 A1 | 6/2010 | Braithwaite et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0168660 A1 | 7/2010 | Galley et al. |
| 2010/0198142 A1 | 8/2010 | Sloan et al. |
| 2010/0256047 A1 | 10/2010 | Sieh et al. |
| 2010/0262434 A1 | 10/2010 | Shaya |
| 2010/0286601 A1 | 11/2010 | Yodfat et al. |
| 2010/0305545 A1 | 12/2010 | Kanderian, Jr. et al. |
| 2010/0324382 A1 | 12/2010 | Cantwell et al. |
| 2010/0331652 A1 | 12/2010 | Groll et al. |
| 2010/0331654 A1 | 12/2010 | Jerdonek et al. |
| 2010/0332142 A1 | 12/2010 | Shadforth et al. |
| 2011/0021894 A1 | 1/2011 | Mohanty et al. |
| 2011/0071365 A1 | 3/2011 | Lee et al. |
| 2011/0071464 A1 | 3/2011 | Palerm |
| 2011/0098548 A1 | 4/2011 | Budiman et al. |
| 2011/0115894 A1 | 5/2011 | Burnett |
| 2011/0119081 A1 | 5/2011 | Vespasiani |
| 2011/0124996 A1 * | 5/2011 | Reinke .............. A61M 5/14248 600/300 |
| 2011/0152830 A1 | 6/2011 | Ruchti et al. |
| 2011/0178008 A1 | 7/2011 | Arai et al. |
| 2011/0213332 A1 | 9/2011 | Mozayeny |
| 2011/0217396 A1 | 9/2011 | Oldani |
| 2011/0218489 A1 | 9/2011 | Mastrototaro et al. |
| 2011/0229602 A1 | 9/2011 | Aymard et al. |
| 2011/0286984 A1 | 11/2011 | Huang |
| 2011/0305771 A1 | 12/2011 | Sampalis |
| 2011/0313674 A1 | 12/2011 | Duke et al. |
| 2011/0319322 A1 | 12/2011 | Bashan et al. |
| 2012/0003339 A1 | 1/2012 | Minacapelli |
| 2012/0022353 A1 | 1/2012 | Bashan et al. |
| 2012/0046606 A1 | 2/2012 | Arefieg |
| 2012/0053222 A1 | 3/2012 | Gorrell et al. |
| 2012/0058942 A1 | 3/2012 | Dupre |
| 2012/0065482 A1 | 3/2012 | Robinson et al. |
| 2012/0095311 A1 | 4/2012 | Ramey et al. |
| 2012/0123234 A1 | 5/2012 | Atlas et al. |
| 2012/0197358 A1 | 8/2012 | Prescott |
| 2012/0213886 A1 | 8/2012 | Gannon et al. |
| 2012/0227737 A1 | 9/2012 | Mastrototaro et al. |
| 2012/0232519 A1 | 9/2012 | Georgiou et al. |
| 2012/0232520 A1 | 9/2012 | Sloan et al. |
| 2012/0238853 A1 | 9/2012 | Arefieg |
| 2012/0244096 A1 | 9/2012 | Xie et al. |
| 2012/0295985 A1 | 11/2012 | Miller et al. |
| 2013/0022592 A1 | 1/2013 | Vaughn et al. |
| 2013/0030358 A1 | 1/2013 | Yodfat et al. |
| 2013/0052285 A1 | 2/2013 | Song et al. |
| 2013/0109620 A1 | 5/2013 | Riis et al. |
| 2013/0144283 A1 | 6/2013 | Barman |
| 2013/0158503 A1 | 6/2013 | Kanderian, Jr. et al. |
| 2013/0165901 A1 | 6/2013 | Ruchti et al. |
| 2013/0190583 A1 | 7/2013 | Grosman et al. |
| 2013/0225683 A1 | 8/2013 | Gagnon et al. |
| 2013/0233727 A1 | 9/2013 | Tsai et al. |
| 2013/0245547 A1 | 9/2013 | El-Khatib et al. |
| 2013/0267796 A1 | 10/2013 | Enric Monte Moreno |
| 2013/0281796 A1 | 10/2013 | Pan |
| 2013/0282301 A1 | 10/2013 | Rush |
| 2013/0289883 A1 | 10/2013 | Bashan et al. |
| 2013/0309750 A1 | 11/2013 | Tajima et al. |
| 2013/0316029 A1 | 11/2013 | Pan et al. |
| 2013/0317316 A1 | 11/2013 | Kandeel |
| 2013/0331323 A1 | 12/2013 | Wu et al. |
| 2013/0338209 A1 | 12/2013 | Gambhire et al. |
| 2013/0345664 A1 | 12/2013 | Beck et al. |
| 2014/0000338 A1 | 1/2014 | Luo et al. |
| 2014/0004211 A1 | 1/2014 | Choi et al. |
| 2014/0024907 A1 | 1/2014 | Howell et al. |
| 2014/0037749 A1 | 2/2014 | Shea et al. |
| 2014/0057331 A1 | 2/2014 | Tajima et al. |
| 2014/0066735 A1 | 3/2014 | Engelhardt et al. |
| 2014/0066888 A1 | 3/2014 | Parikh et al. |
| 2014/0081196 A1 | 3/2014 | Chen |
| 2014/0128706 A1 | 5/2014 | Roy |
| 2014/0170123 A1 | 6/2014 | Alam et al. |
| 2014/0178509 A1 | 6/2014 | Jia |

(56) References Cited

U.S. PATENT DOCUMENTS

| | | |
|---|---|---|
| 2014/0179629 A1 | 6/2014 | Hamaker et al. |
| 2014/0194788 A1 | 7/2014 | Muehlbauer et al. |
| 2014/0213963 A1 | 7/2014 | Wu et al. |
| 2014/0296943 A1 | 10/2014 | Maxik et al. |
| 2014/0297301 A1* | 10/2014 | Rock ............. G06Q 10/103 705/2 |
| 2014/0303466 A1 | 10/2014 | Fitzpatrick et al. |
| 2014/0303552 A1 | 10/2014 | Kanderian, Jr. et al. |
| 2014/0337041 A1 | 11/2014 | Madden et al. |
| 2014/0347491 A1 | 11/2014 | Connor |
| 2014/0349256 A1 | 11/2014 | Connor |
| 2014/0349257 A1 | 11/2014 | Connor |
| 2014/0356420 A1 | 12/2014 | Huang |
| 2014/0363794 A1 | 12/2014 | Angelides |
| 2014/0365534 A1 | 12/2014 | Bousamra et al. |
| 2014/0378381 A1 | 12/2014 | Chen et al. |
| 2014/0378793 A1 | 12/2014 | Kamath et al. |
| 2015/0018633 A1 | 1/2015 | Kovachev et al. |
| 2015/0025496 A1 | 1/2015 | Imran |
| 2015/0025903 A1 | 1/2015 | Mueller-Wolf |
| 2015/0031053 A1 | 1/2015 | Moerman |
| 2015/0037406 A1 | 2/2015 | Martinez et al. |
| 2015/0217053 A1 | 8/2015 | Booth |

FOREIGN PATENT DOCUMENTS

| | | |
|---|---|---|
| AU | 2010330746 A1 | 7/2012 |
| CA | 2519249 A1 | 10/2004 |
| CA | 2670512 A1 | 7/2008 |
| CA | 2720302 A1 | 12/2009 |
| CA | 2720304 A1 | 12/2009 |
| CA | 2733593 A1 | 2/2010 |
| CA | 2752637 A1 | 9/2010 |
| CA | 2761647 A1 | 12/2010 |
| CA | 2766944 A1 | 1/2011 |
| CA | 2784143 A1 | 6/2011 |
| CN | 102016855 A | 4/2011 |
| CN | 102016906 A | 4/2011 |
| CN | 102300501 A | 12/2011 |
| CN | 102395310 A | 3/2012 |
| CN | 102481101 A | 5/2012 |
| CN | 102946804 A | 2/2013 |
| DE | 1082412 T1 | 10/2001 |
| EP | 461207 A1 | 12/1991 |
| EP | 483595 A2 | 5/1992 |
| EP | 557350 A1 | 9/1993 |
| EP | 573499 A1 | 12/1993 |
| EP | 768043 A2 | 4/1997 |
| EP | 862648 A1 | 9/1998 |
| EP | 910578 A2 | 4/1999 |
| EP | 925792 A2 | 6/1999 |
| EP | 1017414 A1 | 7/2000 |
| EP | 1030557 A1 | 8/2000 |
| EP | 1051141 A1 | 11/2000 |
| EP | 1067925 A1 | 1/2001 |
| EP | 1082412 A2 | 3/2001 |
| EP | 1115389 A1 | 7/2001 |
| EP | 483595 | 12/2001 |
| EP | 1173482 A1 | 1/2002 |
| EP | 1185321 A1 | 3/2002 |
| EP | 1196445 A1 | 4/2002 |
| EP | 1214596 A1 | 6/2002 |
| EP | 1305018 A1 | 5/2003 |
| EP | 1317190 A2 | 6/2003 |
| EP | 1382363 A1 | 1/2004 |
| EP | 1424074 A1 | 6/2004 |
| EP | 1482919 A1 | 12/2004 |
| EP | 1581095 A2 | 10/2005 |
| EP | 1610758 A2 | 1/2006 |
| EP | 1679009 A1 | 7/2006 |
| EP | 1698898 A2 | 9/2006 |
| EP | 1773860 A1 | 4/2007 |
| EP | 1846002 A1 | 10/2007 |
| EP | 1885392 A2 | 2/2008 |
| EP | 1915171 A2 | 4/2008 |
| EP | 1921981 A2 | 5/2008 |
| EP | 2114491 A1 | 11/2009 |
| EP | 2129277 A2 | 12/2009 |
| EP | 2139393 A2 | 1/2010 |
| EP | 2170430 A2 | 4/2010 |
| EP | 2257218 A2 | 12/2010 |
| EP | 2260423 A2 | 12/2010 |
| EP | 2260462 A2 | 12/2010 |
| EP | 2276405 A1 | 1/2011 |
| EP | 2300046 A2 | 3/2011 |
| EP | 2328608 A2 | 6/2011 |
| EP | 2352456 A1 | 8/2011 |
| EP | 2355669 A2 | 8/2011 |
| EP | 2377465 A1 | 10/2011 |
| EP | 2384750 A1 | 11/2011 |
| EP | 2393419 A1 | 12/2011 |
| EP | 2400882 A1 | 1/2012 |
| EP | 2418972 A1 | 2/2012 |
| EP | 2442719 A2 | 4/2012 |
| EP | 2448432 A1 | 5/2012 |
| EP | 2448468 A1 | 5/2012 |
| EP | 2448469 A2 | 5/2012 |
| EP | 2482712 A1 | 8/2012 |
| EP | 2516671 A1 | 10/2012 |
| EP | 2518655 A2 | 10/2012 |
| EP | 2525863 A1 | 11/2012 |
| EP | 2535831 A1 | 12/2012 |
| EP | 2552313 A2 | 2/2013 |
| EP | 2582297 A1 | 4/2013 |
| EP | 2585133 A1 | 5/2013 |
| EP | 2590559 A2 | 5/2013 |
| EP | 2596448 A1 | 5/2013 |
| EP | 2603133 A1 | 6/2013 |
| EP | 2605819 A1 | 6/2013 |
| EP | 2640373 A1 | 9/2013 |
| EP | 2641084 A1 | 9/2013 |
| EP | 2644088 A1 | 10/2013 |
| EP | 2654777 A2 | 10/2013 |
| EP | 2659407 A1 | 11/2013 |
| EP | 2666369 A1 | 11/2013 |
| EP | 2685895 A1 | 1/2014 |
| EP | 2720713 A2 | 4/2014 |
| EP | 2736404 A1 | 6/2014 |
| EP | 2742447 A2 | 6/2014 |
| EP | 2742449 A2 | 6/2014 |
| EP | 2745225 A2 | 6/2014 |
| EP | 2760335 A1 | 8/2014 |
| EP | 2763722 A2 | 8/2014 |
| EP | 2798548 A1 | 11/2014 |
| EP | 2822647 A1 | 1/2015 |
| JP | 04800928 B2 | 10/2011 |
| KR | 2011052664 A | 5/2011 |
| KR | 2012047841 A | 5/2012 |
| NO | 2006091918 A2 | 8/2006 |
| NO | 2010075350 A1 | 7/2010 |
| RU | 2011109016 A | 9/2012 |
| WO | 1992019260 A1 | 11/1992 |
| WO | 1996009823 A1 | 4/1996 |
| WO | 1999044496 A1 | 9/1999 |
| WO | 1999063101 A2 | 12/1999 |
| WO | 2002036139 | 5/2002 |
| WO | 2003024468 | 3/2003 |
| WO | 2003077895 | 9/2003 |
| WO | 2003094927 | 11/2003 |
| WO | 2004084820 A2 | 10/2004 |
| WO | 2005041022 A1 | 5/2005 |
| WO | 2005081119 A2 | 9/2005 |
| WO | 2005081170 A2 | 9/2005 |
| WO | 2005081171 A2 | 9/2005 |
| WO | 2005081173 A1 | 9/2005 |
| WO | 2005110222 A1 | 11/2005 |
| WO | 2006022619 A2 | 3/2006 |
| WO | 2006022629 A1 | 3/2006 |
| WO | 2006022633 A1 | 3/2006 |
| WO | 2006022634 A1 | 3/2006 |
| WO | 2006022636 A1 | 3/2006 |
| WO | 2006022638 A1 | 3/2006 |
| WO | 2006044556 A2 | 4/2006 |

(56) References Cited

FOREIGN PATENT DOCUMENTS

| | | |
|---|---|---|
| WO | 2003101177 | 7/2006 |
| WO | 2006079124 A2 | 7/2006 |
| WO | 2006091918 A2 | 8/2006 |
| WO | 2006130901 A1 | 12/2006 |
| WO | 2007116226 A2 | 10/2007 |
| WO | 2007149533 A2 | 12/2007 |
| WO | 2008005761 A2 | 1/2008 |
| WO | 2008013324 A1 | 1/2008 |
| WO | 2008057213 A2 | 5/2008 |
| WO | 2008057384 A2 | 5/2008 |
| WO | 2008067245 A2 | 6/2008 |
| WO | 2008088490 A1 | 7/2008 |
| WO | 2008112078 A2 | 9/2008 |
| WO | 2008124478 A1 | 10/2008 |
| WO | 2009002455 A1 | 12/2008 |
| WO | 2009005960 A2 | 1/2009 |
| WO | 2009075925 A1 | 6/2009 |
| WO | 2009139846 A1 | 11/2009 |
| WO | 2009146119 A2 | 12/2009 |
| WO | 2009146121 A2 | 12/2009 |
| WO | 2010021879 A2 | 2/2010 |
| WO | 2010056718 A2 | 5/2010 |
| WO | 2010089304 A1 | 8/2010 |
| WO | 2010089305 A1 | 8/2010 |
| WO | 2010089306 A1 | 8/2010 |
| WO | 2010089307 A1 | 8/2010 |
| WO | 2010091102 A1 | 8/2010 |
| WO | 2010097796 A1 | 9/2010 |
| WO | 2010135646 A1 | 11/2010 |
| WO | 2010147659 A2 | 12/2010 |
| WO | 2011008520 A2 | 1/2011 |
| WO | 2011037607 A2 | 3/2011 |
| WO | 2011075687 A1 | 6/2011 |
| WO | 2011089600 A1 | 7/2011 |
| WO | 2011094352 A1 | 8/2011 |
| WO | 2011157402 A1 | 12/2011 |
| WO | 2012023964 A1 | 2/2012 |
| WO | 2012047800 A1 | 4/2012 |
| WO | 2012065556 A1 | 5/2012 |
| WO | 2012097064 A1 | 7/2012 |
| WO | 2012122520 A1 | 9/2012 |
| WO | 2012148252 A2 | 11/2012 |
| WO | 2012161670 A2 | 11/2012 |
| WO | 2012177963 A1 | 12/2012 |
| WO | 2013040712 A1 | 3/2013 |
| WO | 2013050309 A1 | 4/2013 |
| WO | 2013086372 A1 | 6/2013 |
| WO | 2013096769 A1 | 6/2013 |
| WO | 2013108262 A1 | 7/2013 |
| WO | 2013134548 A2 | 9/2013 |
| WO | 2013172833 A1 | 11/2013 |
| WO | 2013177565 A1 | 11/2013 |
| WO | 2014011488 A2 | 1/2014 |
| WO | 2014012084 A1 | 1/2014 |
| WO | 2014023834 A2 | 2/2014 |
| WO | 2014024201 A1 | 2/2014 |
| WO | 2014028607 A1 | 2/2014 |
| WO | 2014068007 A1 | 5/2014 |
| WO | 2014075135 | 5/2014 |
| WO | 2014075135 A1 | 5/2014 |
| WO | 2014099829 | 6/2014 |
| WO | 2014099829 A1 | 6/2014 |
| WO | 2014106263 A2 | 7/2014 |
| WO | 2014145049 A2 | 9/2014 |
| WO | 2014149535 | 9/2014 |
| WO | 2014149535 A1 | 9/2014 |
| WO | 2014149781 A1 | 9/2014 |
| WO | 2014152704 A1 | 9/2014 |
| WO | 2014162549 A1 | 10/2014 |
| WO | 2014162549 A1 | 10/2014 |
| WO | 2014164226 A2 | 10/2014 |
| WO | 2014179171 A1 | 11/2014 |
| WO | 2014187812 A1 | 11/2014 |
| WO | 2014190231 A1 | 11/2014 |
| WO | 2014202024 A1 | 12/2014 |
| WO | 2014209630 A2 | 12/2014 |
| WO | 2014209634 A1 | 12/2014 |

OTHER PUBLICATIONS

Vaidya, Anand et al., " Improving the management of diabetes in hospitalized patients: The result of a computer-based house staff training program", Diabetes Technology & Therapeutics, 2012, vol. 14, No. 7, pp. 610-618.

Lee, Joshua et al., "Indication-based ordering: A new paradigm for glycemic control in hospitalized inpatients", Journal of Diabetes Science and Technology, May 2008, vol. 2, Issue 3, pp. 349-356.

Nau, Konrad C. et al., "Glycemic Control in hospitalized patients not in intensive care: Beyond sliding-scale insulin", American Family Physician, May 1, 2010, vol. 81, No. 9, pp. 1130-1133.

International Search Report and Written Opinion for Application No. PCT/US2015/011559 dated Apr. 29, 2015.

International Search Report and Written Opinion for Application No. PCT/US2015/011086 dated Apr. 29, 2015.

International Search Report and Written Opinion for Application No. PCT/US2015/011574 dated Apr. 24, 2015.

* cited by examiner

| New Patient Information | |
|---|---|
| Name: | John Doe |
| Height: | 5' 8" |
| Weight: | 210 |
| Date of Birth: | 4/10/1938 |
| Diabetes History | |
| Age: | 75 |
| Other: | |

IV  SubQ

FIG. 2B

New Patient Information

| Patient Name | | | Patient ID | Room |
|---|---|---|---|---|
| Adkins, Frankie | IV | SubQ | 704563 | 502 |
| Anderson, Mike | IV | SubQ | 705648 | 504 |
| Anton, Mike | IV | SubQ | 712546 | 302 |
| Briggs, George | IV | SubQ | 702589 | 308 |
| Brown, Dan | IV | SubQ | 701112 | 506 |
| Brown, Paul | IV | SubQ | 709895 | 404 |
| Burchfield, John | IV | SubQ | 712544 | 412 |

FIG. 2C

Initial IV Dosing Information — 204a

Initial Multiplier: _____

Target Range:
 Low Limit: _____
 High Limit: _____

IV Meal Bolus   [*]       [ ]
               enable   disable

Standard Hospital meal: _60_ gms of carbohydrate

FIG. 2D

Current Patient (Intravenous) — 116,146

Name: John Doe   Room: 302 (ER)
Patient ID: 7045162   Date of Birth: 4/10/1938 — 208a 230, 230a:
Last BG: 152 mg/dl (Jones, Sue)
Last Insulin Rate: 5.4 units/hr
Target Range: 90-120 mg/dl
Next BG Due: 7/21/2013 at 15:16

Next BG Due:
BG DUE! — 430

(3 Minutes Late) — 432

Alarm Off — 434

Current Patient (Subcutaneous) — 116,146

Name: John Doe   Room: 302 (ER)
Patient ID: 7045162   Date of Birth: 4/10/1938 — 208a 230, 230b:
Basal Insulin: Lantus
Insulin Type: Novolog
Last BG: 151 mg/dl (Jones, Sue)
BG Type: Dinner
Basal Dose: 15 units (1 dose per day)
Next Meal Dose: 5 units Next BG Due:
Lunch — 430

Alarm On — 434

FIG. 4C

Current Patient — 116, 146

Name: John Doe  Room: 302 (ER)
Patient ID: 7045162  Date of Birth: 4/10/1938  — 208a Please enter the current blood glucose value Enter BG Value: [  ] mg/dl Re-Enter BG Value: [  ] mg/dl Is this a pre-meal BG?  ● Yes  ○ No Meal Plan-Number of Carbs Per Meal: [60]

230, 230c

[Cancel] [Continue]

*Caution: Physician order required*

FIG. 4D

Current Patient — 116, 146

Name: John Doe  Room: 302 (ER)
Patient ID: 7045162  Date of Birth: 4/10/1938  — 208a

| Current Insulin | Last BG |
| --- | --- |
| 1.2 Units/hr | 119 mg/dl |

| Target Range | Insulin Concentration |
| --- | --- |
| 90-120 mg/dl | 90-120 mg/dl |

57:33 — 430

[Enter BG] — 436
[Start Meal] — 438

Enter Blood Glucose Value — 116,146

Name: John Doe    Room: 302 (ER)
Patient ID: 7045162    Date of Birth: 4/10/1938 — 208a Please enter the current blood glucose value Enter BG Value: [ ] mg/dl Re-Enter BG Value: [ ] mg/dl Meal Plan-Number of Carbs Per Meal: [60]

[Cancel] [Continue]

*Caution: Physician order required*

Current Patient — 116,146

Name: John Doe    Room: 302 (ER)
Patient ID: 7045162    Date of Birth: 4/10/1938 — 208a

| Current Insulin | Last BG |
|---|---|
| 1.2 Units/hr | 119 mg/dl |

| Target Range | Insulin Concentration |
|---|---|
| 90-120 mg/dl | 90-120 mg/dl |

57:33 — 430

[Enter BG] — 436
[Start Meal] — 438
[Meal Bolus Activated] — 440

Enter Blood Glucose Value — 116,146

Name: John Doe   Room: 302 (ER)
Patient ID: 7045162   Date of Birth: 4/10/1938 — 208a Did the Patient Eat?

○ Yes   ● No

[Cancel] [Continue]

FIG. 5E

Enter Blood Glucose Value — 116,146

Name: John Doe   Room: 302 (ER)
Patient ID: 7045162   Date of Birth: 4/10/1938 — 208a Did the Patient Eat?

● Yes   ○ No

How much did the Patient eat?

○ 25% of Meal   ○ 50% of Meal
○ 75% of Meal   ○ 100% of Meal

○ Actual Number of Carbs: [    ]

[Cancel] [Continue]

FIG. 5F

Start SUBQ Patients — 116, 146

Name: John Doe  Room: 302 (ER)
Patient ID: 7045162  Date of Birth: 4/10/1938 — 208a Transition Patient to SubQ

Warning:
The A1C value of this patient is less than 6. Normally a patient with an A1C of less than 6 does not need to be transitioned to SubQ insulin therapy.

Are you sure you want to continue?

[Cancel] [Yes]

*Caution: Physician order required*

FIG. 6C

Start SUBQ Patients — 116, 146

Name: John Doe  Room: 302 (ER)
Patient ID: 7045162  Date of Birth: 4/10/1938 — 208a After SubQ Transition:

○ Continue patient on Glucommander SubQ

○ Discontinue patient from Glucommander

[Cancel] [Save]

*Caution: Physician order required*

FIG. 6D

Transition Patient to SUBQ — 116, 146

Name: John Doe  Room: 302 (ER)
Patient ID: 7045162  Date of Birth: 4/10/1938 — 208a Transition Patient to SubQ Discontinue IV Insulin  ◯

WARNING:  ◯
Patient is stable. Discontinue IV insulin to prevent hypoglycemia.

Note: Make sure potassium (K) is greater than 4.0...

[Cancel] [Save]

*Caution: Physician order required*

FIG. 6G

INSULIN MANAGEMENT

CROSS REFERENCE TO RELATED APPLICATIONS

This U.S. patent application is a continuation of, and claims priority under 35 U.S.C. § 120 from, U.S. patent application Ser. No. 17/659,652, filed on Apr. 18, 2022, which is a continuation of U.S. patent application Ser. No. 15/856,363, filed on Dec. 28, 2017, which is a continuation of U.S. patent application Ser. No. 15/623,065, filed on Jun. 14, 2017, which is a continuation of U.S. patent application Ser. No. 15/342,102, filed on Nov. 2, 2016, which is a continuation of U.S. patent application Ser. No. 14/511,060, filed on Oct. 9, 2014, which claims priority under 35 U.S.C. § 119(e) to U.S. Provisional Application 61/934,300, filed on Jan. 31, 2014. The disclosures of these prior applications are considered part of the disclosure of this application and are hereby incorporated by reference in their entireties.

TECHNICAL FIELD

This disclosure relates to a system for managing insulin administration or insulin dosing.

BACKGROUND

Today, nearly 40% of patients admitted to acute care hospitals in the United States experience either hyperglycemia or hypoglycemia, both serious medical conditions. Many of these patients have diabetes while others have fluctuating blood sugars due to trauma, drug reactions, stress and other factors. Nurses and doctors managing these patients manually calculate insulin doses using complex paper protocols.

Manual calculation may not be accurate due to human error, which can lead to patient safety issues. Different institutions use multiple and sometimes conflicting protocols to manually calculate an insulin dosage. Moreover, the protocols may include extra paperwork that nurses and physicians have to manage, which in turn leads to workflow inefficiencies, additional operating costs, and employee satisfaction issues. SCIP (Surgical Care Improvement Project) scores, length of stay, readmission and even mortality rates adversely affect sub-optimal glycemic management.

The prevalent method of regulating continuous intravenous insulin infusion is by using a set of written instructions, known as a paper protocol. Paper protocols often involve a tree of conditional statements and some use of tables of numbers, for which a given blood glucose value dictates the use of a different column of insulin rates. The complexity of these paper protocols multiplies the probability of error by the nurses using them. These errors can lead to hypoglycemic events.

SUMMARY

One aspect of the disclosure provides a method of managing insulin. The method includes receiving blood glucose measurements on a computing device from a glucometer. The blood glucose measurements are separated by a time interval. For each time interval, the method includes determining, using the computing device, an intravenous insulin infusion rate based on the blood glucose measurements of the time interval. The method further includes determining, using the computing device, a blood glucose percentage drop based on the blood glucose measurements (e.g., between a current blood glucose measurement and a previous blood glucose measurement). The method further includes determining, using the computing device, a blood glucose drop rate based on the blood glucose measurements and the time interval. The method also includes decreasing the time interval between blood glucose measurements by the glucometer when the blood glucose percentage drop is greater than a threshold percentage drop and decreasing the time interval between blood glucose measurements by the glucometer when the blood glucose drop rate is greater than a threshold drop rate. The method further includes sending the intravenous insulin infusion rate from the computing device to an insulin administration device.

Implementations of the disclosure may include one or more of the following optional features. In some implementations, the method includes setting the time interval between the blood glucose measurements by the glucometer to a default time interval or a minimum of a preconfigured hypoglycemia time interval when a current blood glucose measurement is less than a threshold hypoglycemia blood glucose value. The method includes setting the time interval to a minimum of a preconfigured short time interval when the current blood glucose measurement is greater than the threshold hypoglycemia blood glucose value and less than a lower limit of a blood glucose target range and the blood glucose percentage drop is greater than a low blood glucose percentage drop limit or the current blood glucose measurement is greater than or equal to the lower limit of the blood glucose target range and the blood glucose percentage drop is greater than a regular blood glucose percentage drop limit. In some examples, the method includes setting the time interval to a minimum of a preconfigured blood glucose drop rate time interval when the blood glucose drop rate is greater than a blood glucose drop rate limit, a preconfigured long time interval when the blood glucose measurements have been within the blood glucose target range for a duration of time greater than a stable time period or a preconfigured meal bolus time interval when a meal bolus program is in operation. The preconfigured hypoglycemia time interval is less than the short time interval, the short time interval is less than the blood glucose drop rate time interval, the blood glucose drop rate time interval is less than the long time interval, and the meal bolus time interval is less than the long time interval.

In some examples, the method includes leaving the multiplier unchanged between time intervals when the current blood glucose measurement is greater than an upper limit of a blood glucose target range and a ratio of the current blood glucose measurement divided by a previous blood glucose measurement is less than or equal to a threshold ratio. The method further includes multiplying the multiplier by a change factor when the current blood glucose measurement divided by the previous blood glucose measurement is greater than the threshold ratio. Additionally or alternatively, the method may include the constant being equal to 60 mg/dl and the threshold ratio being equal to 0.85. The method may further include dividing the multiplier by the change factor when the current blood glucose measurement is less than a lower limit of the blood glucose target range.

The method may further include, in response to receiving an indication of patient solid food consumption, increasing the intravenous insulin infusion rate and maintaining the multiplier unchanged for at least two time intervals. In some examples, the method includes receiving, at the computing device, a number of estimated grams of carbohydrates for a meal and determining, using the computing device, an estimated meal bolus in units of insulin based on the number of estimated grams of carbohydrates and a carbohydrate-insulin-ratio. The method may further include determining, using the computing device, an estimated meal bolus insulin rate, based on the estimated meal bolus, an available delivery time, and a configurable constant, and determining, using the computing device, a total insulin rate as a sum of the intravenous insulin rate and the estimated meal bolus insulin rate. The method may further include sending the total insulin rate from the computing device to the insulin administration device. Additionally or alternatively, the method may include dividing a total meal time into meal time sub-intervals, a first meal time sub-interval starting with a pre-meal blood glucose measurement before receiving the indication of patient solid food consumption, and determining, using the computing device, the total insulin rate for each meal time sub-interval in succession.

In some examples, the method includes receiving, at the computing device, a number of actual grams of carbohydrates for the meal during a subsequent time interval after the first time interval and determining, using the computing device, an actual meal bolus based on the number of actual grams of carbohydrates. The method also includes, determining an estimated delivered meal bolus by multiplying the estimated meal bolus rate times an elapsed delivery time. The method may further include determining a remaining meal bolus in units of insulin, using the computing device, by subtracting a product of the estimated delivered meal bolus insulin rate and an actual delivery time from the actual meal bolus. In addition, the method may include determining, using the computing device, a revised meal bolus insulin rate as the remaining meal bolus divided by a time remaining in the total meal time and determining, using the computing device, a revised total insulin rate as a sum of the intravenous insulin rate and the revised meal bolus insulin rate. Further, the method may include sending the revised total insulin rate from the computing device to the insulin administration device. The method may also include decreasing the time interval to less than the default time interval for the one or more meal time sub-intervals.

In some implementations, the method includes electronically displaying on a display in communication with the computing device a warning and blocking transition to a subcutaneous administration of insulin when the current blood glucose measurement is outside a stability target range and electronically displaying on the display a warning when the current blood glucose measurement is within the stability target range for less than a threshold stability period of time. The method may further include determining, using the computing device, a total daily dose of insulin based on the multiplier when the current blood glucose measurement is within a stability target range for a threshold period of time. The method further includes determining, using the computing device, recommended insulin dose comprising a daily basal insulin and a daily meal insulin for subcutaneous therapy as an apportioning of the total daily dose of insulin, wherein the daily basal insulin is half of the total daily dose of insulin and the daily meal insulin is half of the total daily dose of insulin. Further, the method includes sending the recommended insulin does from the computing device to a subcutaneous injection device or electronically displaying the recommended insulin doses on a display in communication with the computing device.

In some examples, when the blood glucose drops more than a threshold percent of its previous value, the method includes decreasing the time interval. This threshold percent is configured with two values: 1) a lower (more sensitive) value when the blood glucose is below the low limit of the target range but above the hypo-threshold; and 2) a higher (less stringent) value when the blood glucose is above the low limit of the target range. The method may include setting the time interval to a hypoglycemia time interval of between about 15 minutes and about 30 minutes when the current blood glucose measurement is below the hypo-threshold blood glucose level.

Implementations of the disclosure may include one or more of the following features. In some implementations, the method determining the insulin dose rate using the current blood glucose measurement, a constant (e.g., 60 mg/dl), and a unit-less multiplier.

The method includes adjusting the multiplier as follows: a) multiplying the multiplier by a change factor when the current blood glucose measurement is greater than an upper limit of the blood glucose target range, and the ratio of the current blood glucose to the previous blood glucose is greater than a threshold-ratio; b) dividing the multiplier by a change factor when the current blood glucose measurement is less than a lower limit of the blood glucose target range; c) re-use the previous multiplier for two or more intervals starting at the manual initiation of a meal bolus infusion process; and d) leaving the multiplier unchanged between time intervals when none of conditions a, b, or c are applicable.

The method includes leaving the multiplier unchanged between time intervals when the current blood glucose measurement is greater than an upper limit of the blood glucose target range and the blood glucose drop rate is greater than or equal to a threshold rate of descent, and multiplying the multiplier by a change factor when the current blood glucose measurement is greater than an upper limit of the blood glucose target range and the blood glucose drop rate is less than the threshold rate of descent. Additionally or alternatively, the method includes dividing the multiplier by a change factor when the current blood glucose measurement is less than a lower limit of a blood glucose target range and leaving the multiplier unchanged between time intervals when the current blood glucose measurement is within the blood glucose target range. In some examples, the method includes leaving the multiplier unchanged for at least two subsequent time intervals when the current blood glucose measurement is a pre-meal measurement.

In some examples, a meal bolus infusion process allows for the calculation of mealtime insulin for patients consuming oral carbohydrates. These examples may include leaving the multiplier unchanged for at least two subsequent time intervals when the current blood glucose measurement is a pre-meal measurement. In some examples, the method includes receiving, on the computing device, a number of carbohydrates for a meal and determining, using the computing device, a meal bolus rate based on the number of carbohydrates and an intravenous insulin rate based on the blood glucose level. In addition, the method includes determining a Total Insulin Rate including the sum of the meal bolus rate and the intravenous insulin rate based on a blood glucose value. The method may further include setting the time interval to about 30 minutes immediately following the pre-meal blood glucose and for the next glucose measurement time interval. If the blood glucose measurement is a second consecutive measurement after an initial pre-meal blood glucose measurement, the method includes setting the time interval to about 60 minutes.

In some implementations, the method includes decreasing the time interval when the current blood glucose measurement is greater than or equal to the lower limit of the blood glucose target range and the blood glucose drop rate exceeds a threshold drop rate. The method may also include setting the time interval to a default value of about one hour when the current blood glucose measurement is greater than or equal to the lower limit of the blood glucose target range and the blood glucose drop rate is less than or equal to a threshold drop rate. The method may include setting the time interval to a hypoglycemia time interval of between about 15 minutes and about 30 minutes, when the current blood glucose measurement is below the lower limit of the blood glucose target range and greater than a hypo-threshold blood glucose level.

In some implementations, the method includes decreasing the time interval when the current blood glucose measurement is below the lower limit of the blood glucose target range and below the hypo-threshold blood glucose level, and the blood glucose drop rate is less than or equal to a threshold drop rate. The method may also include setting the time interval to a default value of about one hour when the current blood glucose measurement is below the lower limit of the blood glucose target range and below the hypo-threshold blood glucose level, and the blood glucose drop rate is greater than the threshold drop rate.

In some examples, the method includes receiving, on the computing device, a number of carbohydrates per meal and determining, using the computing device, an intravenous insulin rate. In addition, the method includes determining, using the computing device, a meal bolus rate based on the number of carbohydrates and the insulin dose rate based on the intravenous insulin rate and the estimated meal bolus rate. The method may further include setting the time interval to about 30 minutes. If the blood glucose measurement is a second consecutive measurement after an initial pre-meal blood glucose measurement, the method includes setting the time interval to about minutes.

In some implementations, the method includes a function to transition the insulin delivery method from an intravenous to subcutaneous basal-bolus regimen. The transition method provides doses and parameters for starting the patient on basal-bolus subcutaneous treatment. The transition method includes electronically displaying on a display a warning and blocking transition to a subcutaneous administration of insulin when the current blood glucose measurement is outside a stability target range. In addition, the method includes electronically displaying on the display a warning when the current blood glucose measurement is within the stability target range for less than a threshold stability period of time. In some examples, the method includes determining a total daily dose of insulin based on the multiplier when the current blood glucose measurement is within a stability target range for a threshold stability period of time. Another aspect of the disclosure includes a system for managing insulin. The system includes a glucometer measuring blood glucose measurements separated by a time interval, an insulin administration device, and a dosing controller in communication with the glucometer and the insulin administration device. The dosing controller includes a computing device and non-transitory memory in communication with the computing device. The non-transitory memory stores instructions that when executed by the computing device cause the computing device to perform operations. The operations include receiving blood glucose measurements on a computing device from a glucometer, the blood glucose measurements separated by a time interval. For each time interval, the system includes determining, using the computing device, an intravenous insulin infusion rate based on the blood glucose measurements of the time interval and determining, using the computing device, a blood glucose percentage drop based on the blood glucose measurements (e.g., between a current blood glucose measurement and a previous blood glucose measurement). The system further includes determining, using the computing device, a blood glucose drop rate based on the blood glucose measurements and the time interval and decreasing the time interval between blood glucose measurements by the glucometer when the blood glucose percentage drop is greater than a threshold percentage drop. The system further includes decreasing the time interval between blood glucose measurements by the glucometer when the blood glucose drop rate is greater than a threshold drop rate and sending the intravenous insulin infusion rate from the computing device to the insulin administration device.

In some implementations, the system operations further include setting the time interval between the blood glucose measurements by the glucometer to a default time interval or a minimum of a preconfigured hypoglycemia time interval when a current blood glucose measurement is less than a threshold hypoglycemia blood glucose value or a preconfigured short time interval. The minimum of a preconfigured short time interval is set when the current blood glucose measurement is greater than the threshold hypoglycemia blood glucose value and less than a lower limit of a blood glucose target range and the blood glucose percentage drop is greater than a low blood glucose percentage drop limit or the current blood glucose measurement is greater than or equal to the lower limit of the blood glucose target range and the blood glucose percentage drop is greater than a regular blood glucose percentage drop limit. Further, the operations include setting the time interval between the blood glucose measurements by the glucometer to a minimum of a preconfigured blood glucose drop rate time interval when the blood glucose drop rate is greater than a blood glucose drop rate limit or a preconfigured long time interval when the blood glucose measurements have been within the blood glucose target range for a duration of time greater than a stable time period, or a preconfigured meal bolus time interval when a meal bolus program is in operation. The preconfigured hypoglycemia time interval is less than the short time interval, the short time interval is less than the blood glucose drop rate time interval, the blood glucose drop rate time interval is less than the long time interval, and the meal bolus time interval is less than the long time interval.

In some examples, the operations further include leaving the multiplier unchanged between time intervals when the current blood glucose measurement is greater than an upper limit of a blood glucose target range and a ratio of the current blood glucose measurement divided by a previous blood glucose measurement is less than or equal to a threshold ratio. The system further includes multiplying the multiplier by a change factor when the current blood glucose measurement is greater than the upper limit of the blood glucose target range and the ratio of the current blood glucose measurement divided by the previous blood glucose measurement is greater than the threshold ratio. In some examples, the constant equals 60 mg/dl and the threshold ratio is 0.85. Additionally or alternatively, the operations may further include dividing the multiplier by the change factor when the current blood glucose measurement is less than a lower limit of the blood glucose target range. In some implementations, the operations further include, in response to receiving an indication of patient solid food consumption, increasing the intravenous insulin infusion rate and maintaining the multiplier unchanged for at least two time intervals.

The system may further include receiving, at the computing device, a number of estimated grams of carbohydrates for a meal, determining, using the computing device, an estimated meal bolus in units of insulin based on the number of estimated grams of carbohydrates and a carbohydrate-insulin-ratio and determining, using the computing device, an estimated meal bolus insulin rate, based on the estimated meal bolus, an available delivery time, and a configurable constant. The system may also include determining, using the computing device, a total insulin rate as a sum of the intravenous insulin rate and the estimated meal bolus insulin rate and sending the total insulin rate from the computing device to the insulin administration device. The system operations may further include dividing a total meal time into meal time sub-intervals, a first meal time sub-interval starting with a pre-meal bolus glucose measurement before receiving the indication of patient solid food consumption and determining, using the computing device, the total insulin rate for each meal time sub-interval in succession.

In some examples, the operations further include receiving, at the computing device, a number of actual grams of carbohydrates for the meal during a subsequent time interval after the first time interval, determining, using the computing device, an actual meal bolus based on the number of actual grams of carbohydrates and determining a meal bolus in units of insulin, using the computing device, by subtracting a product of the estimated meal bolus insulin rate and an actual delivery time from the actual meal bolus. The system may further include determining, using the computing device, a revised meal bolus insulin rate as the remaining meal bolus divided by a time remaining in the total meal time, determining, using the computing device, a revised total insulin rate as a sum of the intravenous insulin rate and the revised meal bolus insulin rate and sending the revised total insulin rate from the computing device to the insulin administration device. The operations may further comprise decreasing the time interval to less than the default time interval for the one or more meal time sub-intervals.

In some implementations, the operations include electronically displaying on a display in communication with the computing device a warning and blocking transition to a subcutaneous administration of insulin when the current blood glucose measurement is outside a stability target range and electronically displaying on the display a warning when the current blood glucose measurement is within the stability target range for less than a threshold stability period of time. In some examples, the operations include determining, using the computing device, a total daily dose of insulin based on the multiplier when the current blood glucose measurement is within a stability target range for a threshold stability period of time. The system also includes determining, using the computing device, recommended insulin dose including a daily basal insulin and a daily meal insulin for subcutaneous therapy as an apportioning of the total daily dose of insulin, wherein the daily basal insulin is half of the total daily dose of insulin and the daily meal insulin is half of the total daily dose of insulin. The system may further include sending the recommended insulin dose from the computing device to a subcutaneous injection device or electronically displaying the recommended insulin doses on a display in communication with the computing device.

The dosing controller may determine the insulin dose rate based on the current blood glucose measurement, a constant (e.g., 60 mg/dl), and a multiplier. The dosing controller leaves the multiplier unchanged between time intervals when the current blood glucose measurement is greater than an upper limit of the blood glucose target range and the blood glucose drop rate is greater than or equal to a threshold rate of descent. In addition, the dosing controller multiplies the multiplier by a change factor when the current blood glucose measurement is greater than an upper limit of the blood glucose target range and the blood glucose drop rate is less the threshold rate of descent. The dosing controller may leave the multiplier unchanged between time intervals when the current blood glucose measurement is less than a lower limit of the blood glucose target range, and it may divide the multiplier by a change factor when the current blood glucose measurement is within the blood glucose target range. In some examples, the dosing controller leaves the multiplier unchanged for at least two subsequent time intervals when the current blood glucose measurement is a pre-meal measurement.

In some implementations, the dosing controller decreases the time interval when the current blood glucose measurement is greater than or equal to the lower limit of the blood glucose target range and the blood glucose drop rate exceeds a threshold drop rate. In addition, the dosing controller sets the time interval to a default value of about one hour when the current blood glucose measurement is greater than or equal to the lower limit of the blood glucose target range and the blood glucose drop rate is less than or equal to a threshold drop rate. The dosing controller may set the time interval to a hypoglycemia time interval of between about 15 minutes and about 30 minutes, when the current blood glucose measurement is below the lower limit of the blood glucose target range and greater than a hypo-threshold blood glucose level.

In some examples, the dosing controller decreases the time interval when the current blood glucose measurement is below the lower limit of the blood glucose target range and below the hypo-threshold blood glucose level, and the blood glucose drop rate is less than or equal to a threshold drop rate. Moreover, the dosing controller sets the time interval to a default value of about one hour when the current blood glucose measurement is below the lower limit of the blood glucose target range and below the hypo-threshold blood glucose level, and the blood glucose drop rate is greater than the threshold drop rate.

In some examples, the dosing controller receives, on the computing device, a number of carbohydrates per meal, then determines, using the computing device, an intravenous insulin rate and a meal bolus rate based on the number of carbohydrates. Furthermore, the dosing controller determines, using the computing device, the insulin dose rate based on the intravenous insulin rate and the estimated meal bolus rate. The dosing controller may set the time interval to about 30 minutes. Additionally or alternatively, the dosing controller may set the time interval to about 60 minutes if the blood glucose measurement is a second consecutive measurement after an initial pre-meal blood glucose measurement.

In some examples, the dosing controller electronically displays on a display in communication with the dosing controller a warning and blocks transition to a subcutaneous administration of insulin when the current blood glucose measurement is outside a stability target range. The dosing controller electronically displays on the display a warning when the current blood glucose measurement is within the stability target range for less than a threshold stability period of time. The dosing controller may determine a total daily dose of insulin based on the multiplier when the current blood glucose measurement is within a stability target range for a threshold stability period of time.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2B is a schematic view of an exemplary display for inputting patient information.

FIG. 2C is a schematic view of an exemplary display for selecting a patient from a list of patients.

FIG. 2D is a schematic view of an exemplary display indicating initial intravenous dosing information.

FIGS. 4B and 4C are schematic views of an exemplary display showing the time a next blood glucose measurement is due.

FIG. 4D is a schematic view of an exemplary display for inputting patient information.

FIG. 4E is a schematic view of an exemplary display of patient information and a timer for a patient's next blood glucose measurement.

FIG. 5C is a schematic view of an exemplary display for inputting a patient's blood glucose measurement.

FIG. 5D is a schematic view of an exemplary display of patient information and a timer for a patient's next blood glucose measurement.

FIGS. 5E and 5F are schematic views of exemplary displays requesting information from the user.

FIG. 6C is a schematic view of an exemplary warning to the user relating to the patient.

FIG. 6D is a schematic view of an exemplary display inquiring whether the patient should continue treatment or stop.

FIG. 6G is a schematic view of an exemplary view to the user relating to transitioning a patient to subcutaneous delivery.

Like reference symbols in the various drawings indicate like elements.

DETAILED DESCRIPTION

Diabetic hospital patients who eat meals often have poor appetites; consequently, co-ordination of meal boluses and meals is difficult. Meal boluses without meals cause hypoglycemia; meals without meal boluses cause hyperglycemia. Different providers may use different methods of adjusting doses: some may use formulas of their own; some may use paper protocols that are complex and difficult for the nurse to follow, leading to a high incidence of human error; and some may use heuristic methods. There is no guarantee of consistency. Moreover, for diabetic patients who do not eat meals, there is no currently no computerized method of tracking the patient's status. For non-diabetic patient who get include due to "stress hyperglycemia" when they are very sick or undergoing surgery, there is no current method of monitoring their recovery when the stress subsides and their need for insulin rapidly decreases. If the dose regimen does not decrease rapidly also, hypoglycemia may result. Therefore, it is desirable to have a clinical support system 100 (FIGS. 1A and 1B) that monitors patients' blood glucose level.

Figure 1A:
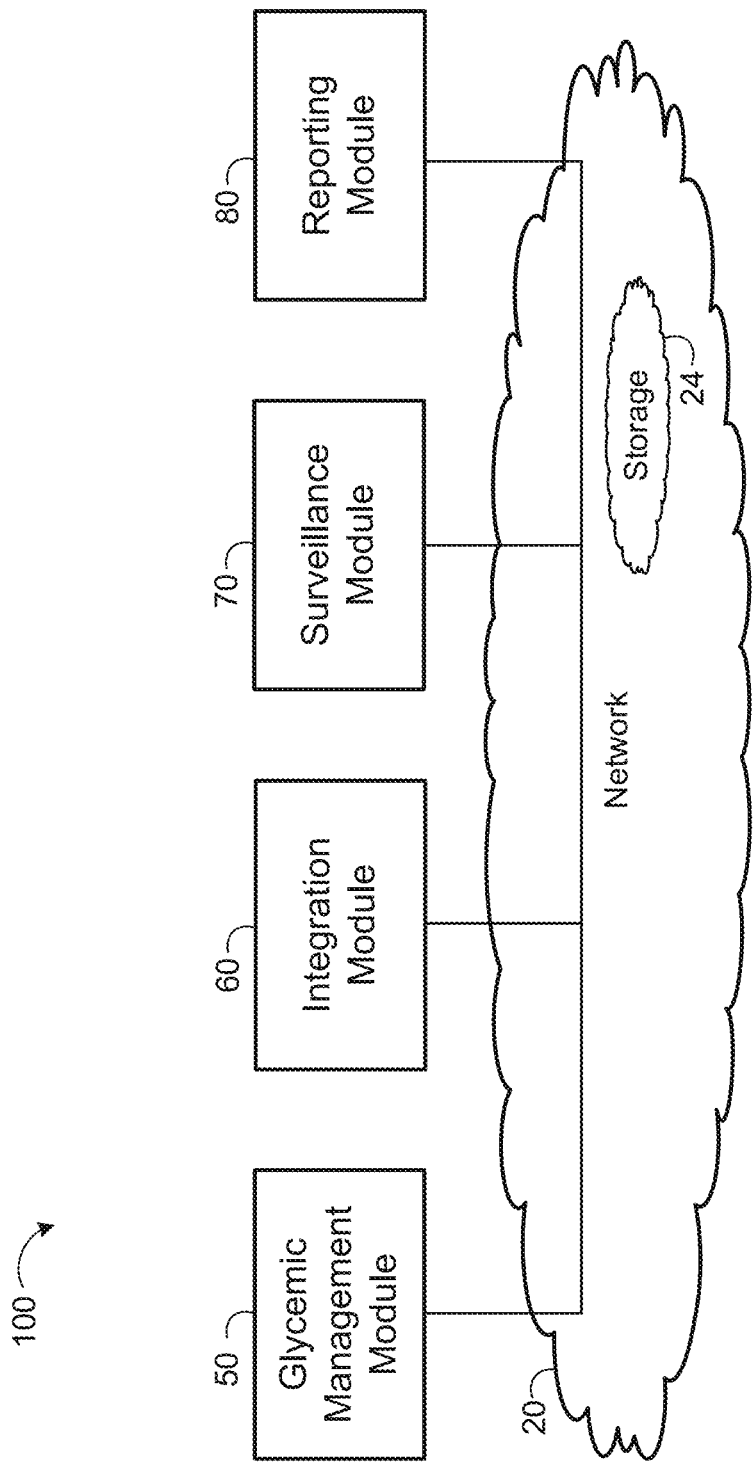
FIG. 1A is a schematic view of an exemplary system for monitoring blood glucose level of a patient.
Figure 1B:
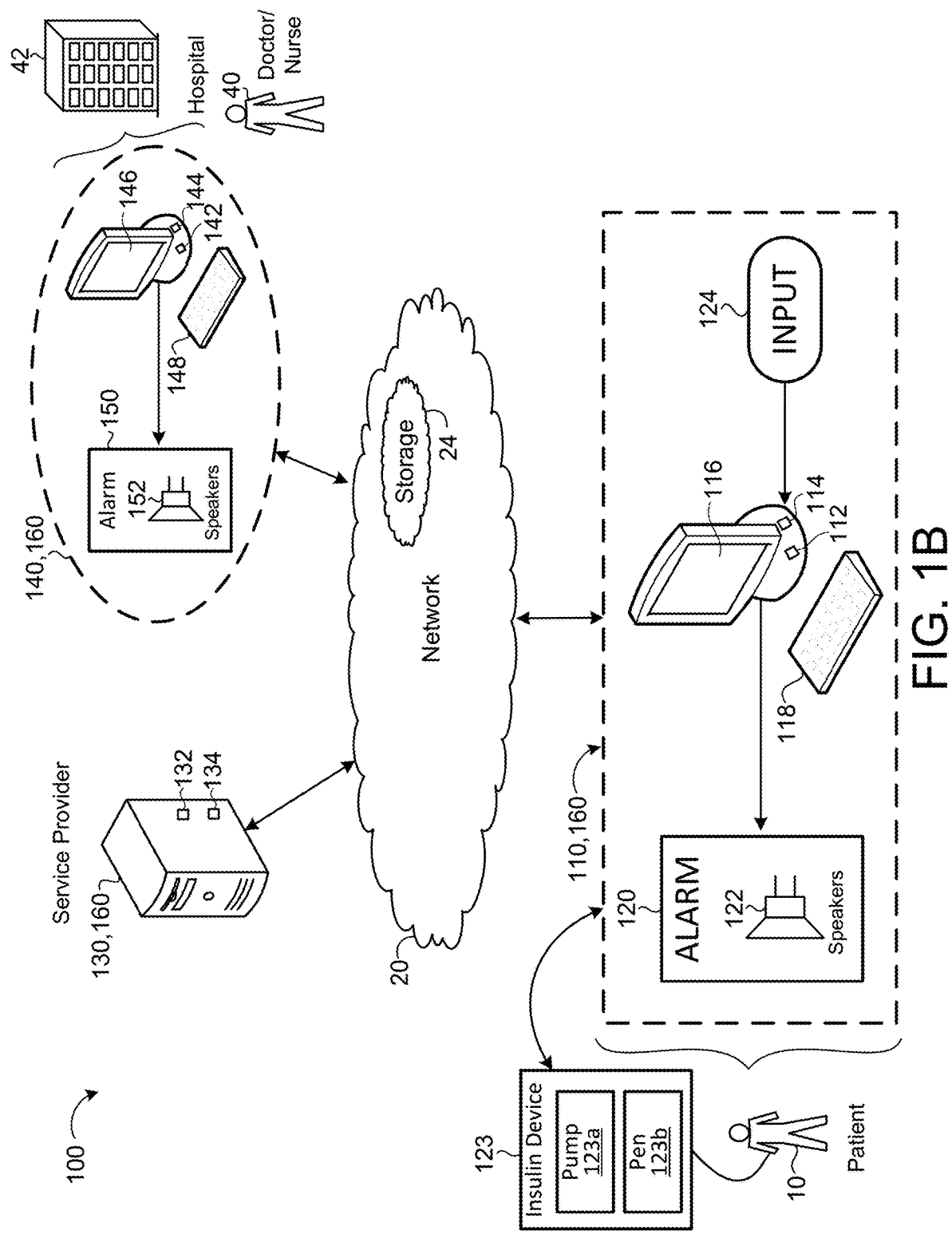
FIG. 1B is a schematic view of an exemplary system for monitoring blood glucose level of a patient.

Referring to FIGS. 1A and 1B, in some implementations, a clinical decision support system 100 analyzes inputted patient condition parameters for a patient 10 and calculates a personalized dose of insulin to bring and maintain the patient's blood glucose level into a target range $BG_{TR}$. Moreover, the system 100 monitors the glucose levels of a patient 10 and calculates recommended intravenous or subcutaneous insulin dose to bring the patient's blood glucose into the preferred target range $BG_{TR}$ over a recommended period of time. A qualified and trained healthcare professional 40 may use the system 100 along with clinical reasoning to determine the proper dosing administered to a patient 10. Therefore, the system 100 is a glycemic management tool for evaluation a patient's current and cumulative blood glucose value BG while taking into consideration the patient's information such as age, weight, and height. The system 100 may also consider other information such as carbohydrate content of meals, insulin doses being administered to the patient 10, e.g., long-acting insulin doses for basal insulin and rapid-acting insulin doses for meal boluses and correction boluses. Based on those measurements (that may be stored in non-transitory memory 24, 114, 144), the system 100 recommends an intravenous dosage of insulin, glucose, or saline or a subcutaneous basal and bolus insulin dosing recommendation or prescribed dose to adjust and maintain the blood glucose level towards a configurable (based on the patient's information) physician's determined blood glucose target range $BG_{TR}$. The system 100 also considers a patient's insulin sensitivity or improved glycemic management and outcomes. The system 100 may take into account pertinent patient information such as demographics and previous results, leading to a more efficient use of healthcare resources. Finally, the system 100 provides a reporting platform for reporting the recommendations or prescribed dose(s) to the user 40 and the patient 10. In addition, for diabetic patients who eat meals, the system 100 provides faster, more reliable, and more efficient insulin administration than a human monitoring the insulin administration. The system 100 reduces the probability of human error and insures consistent treatment, due to the system's capability of storing and tracking the patient's blood glucose levels BG, which may be used for statistical studies. As for patients who are tube-fed or do not eat meals, the system 100 provides dedicated subprograms, which in turn provide basal insulin and correction boluses but no meal boluses. Patients who are tube-fed or who do not eat usually have a higher basal insulin level than patients who eat, because the carbohydrates in the nutritive formula are accounted—for in the basal insulin. The system 100 provides a meal-by-meal adjustment of Meal Boluses without carbohydrate counting, by providing a dedicated subprogram that adjusts meal boluses based on the immediately preceding meal bolus and the BG that followed it. The system 100 provides a meal-by-meal adjustment of Meal Boluses with carbohydrate counting by providing a dedicated subprogram that adjusts meal boluses based a Carbohydrate-to-Insulin Ratio (CIR) that is adjusted at each meal, based on the CIR used at the immediately preceding meal bolus and the BG that followed it.

Hyperglycemia is a condition that exists when blood sugars are too high. While hyperglycemia is typically associated with diabetes, this condition can exist in many patients who do not have diabetes, yet have elevated blood sugar levels caused by trauma or stress from surgery and other complications from hospital procedures. Insulin therapy is used to bring blood sugar levels back into a normal range.

Hypoglycemia may occur at any time when a patient's blood glucose level is below a preferred target. Appropriate management of blood glucose levels for critically ill patients reduces co-morbidities and is associated with a decrease in infection rates, length of hospital stay, and death. The treatment of hyperglycemia may differ depending on whether or not a patient has been diagnosed with Type 1 diabetes mellitus, Type 2 diabetes mellitus, gestational diabetes mellitus, or non-diabetic stress hyperglycemia. The blood glucose target range $BG_{TR}$ is defined by a lower limit, i.e., a low target $BG_{TRL}$ and an upper limit, i.e., a high target $BG_{TRH}$.

Stress-related hyperglycemia: Patients often get "stress hyperglycemia" if they are very sick or undergoing surgery. This condition requires insulin. In diabetic patients, the need for insulin is visibly increased. In non-diabetic patients, the stress accounts for the only need for insulin, and as the patients recover, the stress subsides, and their need for insulin rapidly decreases. For non-diabetic patients, the concern is that their need for insulin decreases faster than their dose regimen, leading to hypoglycemia.

Diabetes Mellitus has been treated for many years with insulin. Some recurring terms and phrases are described below:

Injection: Administering insulin by means of manual syringe or an insulin "pen," with a portable syringe named for its resemblance to the familiar writing implement.

Infusion: Administering insulin in a continuous manner by means of an insulin pump for subcutaneous insulin or an intravenous apparatus 123a, both of which are capable of continuous administration.

Intravenous Insulin Therapy: Intravenous infusion of insulin has been approved by the U.S. Food and Drug Administration as an acceptable indication for use. Intravenous infusion is the fastest of all insulin administration routes and, typically, only available in the hospital setting. For instance, in intensive care units, the patients may be fed by intravenous glucose infusion, by intravenous Total Parenteral Nutrition (TPN), or by a tube to the stomach. Patients are often given insulin in an intravenous infusion at an insulin infusion rate IIR. The IIR is regulated by the frequent testing of blood glucose, typically at intervals between about 20 minutes and 2 hours. This is combined with a protocol in which a new IIR is computed after each blood glucose test.

Basal-Bolus Therapy: Basal-bolus therapy is a term that collectively refers to any insulin regimen involving basal insulin and boluses of insulin.

Basal Insulin: Insulin that is intended to metabolize the glucose released by a patient's the liver during a fasting state. Basal insulin is administered in such a way that it maintains a background level of insulin in the patient's blood, which is generally steady but may be varied in a programmed manner by an insulin pump 123a. Basal insulin is a slow, relatively continuous supply of insulin throughout the day and night that provides the low, but present, insulin concentration necessary to balance glucose consumption (glucose uptake and oxidation) and glucose production (glucogenolysis and gluconeogenesis). A patient's Basal insulin needs are usually about 10 to 15 mU/kg/hr and account for 30% to 50% of the total daily insulin needs; however, considerable variation occurs based on the patient 10.

Bolus Insulin: Insulin that is administered in discrete doses. There are two main types of boluses, Meal Bolus and Correction Bolus.

Meal Bolus: Taken just before a meal in an amount which is proportional to the anticipated immediate effect of carbohydrates in the meal entering the blood directly from the digestive system. The amounts of the Meal Boluses may be determined and prescribed by a physician 40 for each meal during the day, i.e., breakfast, lunch, and dinner. Alternatively, the Meal Bolus may be calculated in an amount generally proportional to the number of grams of carbohydrates in the meal. The amount of the Meal Bolus is calculated using a proportionality constant, which is a personalized number called the Carbohydrate-to-Insulin Ratio (CIR) and calculated as follows:

$$\text{Meal Insulin Bolus} = \{\text{grams of carbohydrates in the meal}\}/\text{CIR} \quad (1)$$

Correction Bolus CB: Injected immediately after a blood glucose measurement; the amount of the correction bolus is proportional to the error in the BG (i.e., the bolus is proportional to the difference between the blood glucose measurement BG and the patient's personalized Target blood glucose $BG_{Target}$). The proportionality constant is a personalized number called the Correction Factor, CF, and is calculated as follows:

$$CB = (BG - BG_{Target})/CF \quad (2)$$

A Correction Bolus CB is generally administered in a fasting state, after the previously consumed meal has been digested. This often coincides with the time just before the next meal.

There are several kinds of Basal-Bolus insulin therapy including Insulin Pump therapy and Multiple Dose Injection therapy:

Insulin Pump Therapy: An insulin pump 123a is a medical device used for the administration of insulin in the treatment of diabetes mellitus, also known as continuous subcutaneous insulin infusion therapy. The device includes: a pump, a disposable reservoir for insulin, and a disposable infusion set. The pump 123a is an alternative to multiple daily injections of insulin by insulin syringe or an insulin pen and allows for intensive insulin therapy when used in conjunction with blood glucose monitoring and carbohydrate counting. The insulin pump 123a is a battery-powered device about the size of a pager. It contains a cartridge of insulin, and it pumps the insulin into the patient via an "infusion set", which is a small plastic needle or "canula" fitted with an adhesive patch. Only rapid-acting insulin is used.

Multiple Dose Injection (MDI): MDI involves the subcutaneous manual injection of insulin several times per day using syringes or insulin pens 123b. Meal insulin is supplied by injection of rapid-acting insulin before each meal in an amount proportional to the meal. Basal insulin is provided as a once, twice, or three time daily injection of a dose of long-acting insulin. Other dosage frequencies may be available. Advances continue to be made in developing different types of insulin, many of which are used to great advantage with MDI regimens:

Long-acting insulins are non-peaking and can be injected as infrequently as once per day. These insulins are widely used for Basal Insulin. They are administered in dosages that make them appropriate for the fasting state of the patient, in which the blood glucose is replenished by the liver to maintain a steady minimum blood glucose level.

Rapid-acting insulins act on a time scale shorter than natural insulin. They are appropriate for boluses.

In some examples, critically ill patients are ordered nil per os (NPO), which means that oral food and fluids are withheld from the patient 10. Typically these patients are unconscious, have just completed an invasive surgical procedure, or generally have difficulty swallowing. Intravenous insulin infusion is typically the most effective method of managing blood glucose levels in these patients. A patient 10 may be NPO and receiving a steady infusion of intravenous glucose, Total Parenteral Nutrition, tube feeding, regular meals that include carbohydrates, or not receiving any nutrition at all. In cases where the patient 10 is not receiving any nutrition, blood glucose is typically replaced by endogenous production by the liver.

As a patient's condition improves, an NPO order may be lifted, allowing the patient 10 to commence an oral caloric intake. In patients 10 with glycemic abnormalities, additional insulin may be needed to cover the consumption of carbohydrates. These patients 10 generally receive one-time injections of insulin in the patient's subcutaneous tissue.

Subcutaneous administration of mealtime insulin in critically ill patients 10 can introduce a patient safety risk if, after receiving the insulin injection, the patient 10 decides not to eat, is unable to finish the meal, or experiences emesis.

Continuous intravenous infusion of mealtime insulin, over a predetermined time interval, allows for an incremental fulfillment of the patient's mealtime insulin requirement, while minimizing patient safety risks. If a patient 10 decides he/she is unable to eat, the continuous intravenous infusion may be stopped or, if a patient 10 is unable to finish the meal, the continuous intravenous infusion rate may be decreased to compensate for the reduction in caloric intake.

The pharmacokinetics (what the body does to a drug over a period of time, which includes the processes of absorption, distribution, localization in tissues, biotransformation, and excretion) and pharmacodynamics (what a drug does to the body) actions of insulin significantly improve when administering insulin via an intravenous route, which is a typical method of delivery for hospitalized patients 10. The management of prandial insulin requirements using an intravenous route can improve patient safety, insulin efficiency, and the accuracy of insulin dosing. The majority of patients who require continuous intravenous insulin infusion therapy may also need to be transitioned to a subcutaneous insulin regimen for ongoing control of blood glucose, regardless of diabetes mellitus (DM) diagnosis. Moreover, the timing, dosing, and process to transition patients 10 from a continuous intravenous route of insulin administration to a subcutaneous insulin regimen is complex and should be individualized based on various patient parameters. Failure to individualize this approach could increase the risk of severe hypoglycemia during the transition process. If not enough insulin is given, the patient 10 may experience acute post-transition hyperglycemia, requiring re-initiation of a continuous intravenous insulin infusion. Therefore, the clinical decision support system 100 calculates a personalized dose of insulin to bring and maintain the patient's blood glucose level into a target range $BG_{TR}$, while taking into consideration the condition of the patient 10.

The clinical decision support system 100 includes a glycemic management module 50, an integration module 60, a surveillance module 70, and a reporting module 80. Each module 50, 60, 70, 80 is in communication with the other modules 50, 60, 70, 80 via a network 20. In some examples, the network 24 (discussed below) provides access to cloud computing resources that allows for the performance of services on remote devices instead of the specific modules 50, 60, 70, 80. The glycemic management module 50 executes a process 200 (e.g., an executable instruction set) on a processor 112, 132, 142 or on the cloud computing resources. The integration module 60 allows for the interaction of users 40 with the system 100. The integration module 60 receives information inputted by a user 40 and allows the user 40 to retrieve previously inputted information stored on a storage system (e.g., one or more of cloud storage resources 24, a non-transitory memory 144 of a hospital's electronic medical system 140, a non-transitory memory 114 of the patient device 110, or other non-transitory storage media in communication with the integration module 60). Therefore, the integration module 60 allows for the interaction between the users 40 and the system 100 via a display 116, 146. The surveillance module 70 considers patient information 208a received from a user 40 via the integration module 60 and information received from a glucometer 124 that measures a patient's blood glucose value BG and determines if the patient 10 is within a threshold blood glucose value $BU_{TH}$. In some examples, the surveillance module 70 alerts the user 40 if a patient's blood glucose values BG are not within a threshold blood glucose value $BG_{TH}$. The surveillance module 70 may be preconfigured to alert the user of other discrepancies between expected values and actual values based on preconfigured parameters (discussed below). For example, when a patient's blood glucose value BG drops below a lower limit of the threshold blood glucose value $BG_{THL}$. The reporting module 80 may be in communication with at least one display 116, 146 and provides information to the user 40 determined using the glycemic management module the integration module 60, and/or the surveillance module 70. In some examples, the reporting module 80 provides a report that may be displayed on a display 116, 146 and/or is capable of being printed.

The system 100 is configured to evaluate a glucose level and nutritional intake of a patient 10. The system 100 also evaluates whether the patient 10 is transitioning to a subcutaneous insulin regime. Based on the evaluation and analysis of the data, the system 100 calculates an insulin dose, which is administered to the patient 10 to bring and maintain the blood glucose level of the patient 10 into the blood glucose target range $BG_{TR}$. The system 100 may be applied to various devices, including, but not limited to, intravenous infusion pumps 123a, subcutaneous insulin infusion pumps 123a, glucometers, continuous glucose monitoring systems, and glucose sensors. In some implementations, as the system 100 is monitoring the patient's blood glucose values BG and the patient's insulin intake, the system 100 notifies the user 40 if the patient 10 receives more than 500 units/hour of insulin because the system 100 considers these patients 10 to be insulin resistant.

In some examples the clinical decision support system 100 includes a network 20, a patient device 110, a dosing controller 160, and a service provider 130. The patient device 110 may include, but is not limited to, desktop computers or portable electronic device (e.g., cellular phone, smartphone, personal digital assistant, barcode reader, personal computer, or a wireless pad) or any other electronic device capable of sending and receiving information via the network 20.

The patient device 110 includes a data processor 112 (e.g., a computing device that executes instructions), and non-transitory memory 114 and a display 116 (e.g., touch display or non-touch display) in communication with the data processor 112. In some examples, the patient device 110 includes a keyboard 118, speakers 212, microphones, mouse, and a camera.

The service provider 130 may include a data processor 132 in communication with non-transitory memory 134. The service provider 130 provides the patient 10 with a process 200 (see FIG. 2) (e.g., a mobile application, a web-site application, or a downloadable program that includes a set of instructions) executable on a processor 112, 132, 142 of the dosing controller 160 and accessible through the network 20 via the patient device 110, intravenous infusion pumps 123a, hospital electronic medical record systems 140, or portable blood glucose measurement devices 124 (e.g., glucose meter or glucometer). Intravenous infusion pumps infuse fluids, medication or nutrients into a patient's circulatory system. Intravenous infusion pumps 123a may be used intravenously and, in some instances, subcutaneous, arterial and epidural infusions are used. Intravenous infusion pumps 123a typically administer fluids that are expensive or unreliable if administered manually (e.g., using a pen 123b) by a nurse or doctor 40. Intravenous infusion pumps 123a can administer a 0.1 ml per hour injection, injections every minute, injections with repeated boluses requested by the patient, up to a maximum number per hours, or fluids whose volumes vary by the time of day.

Figure 2A:
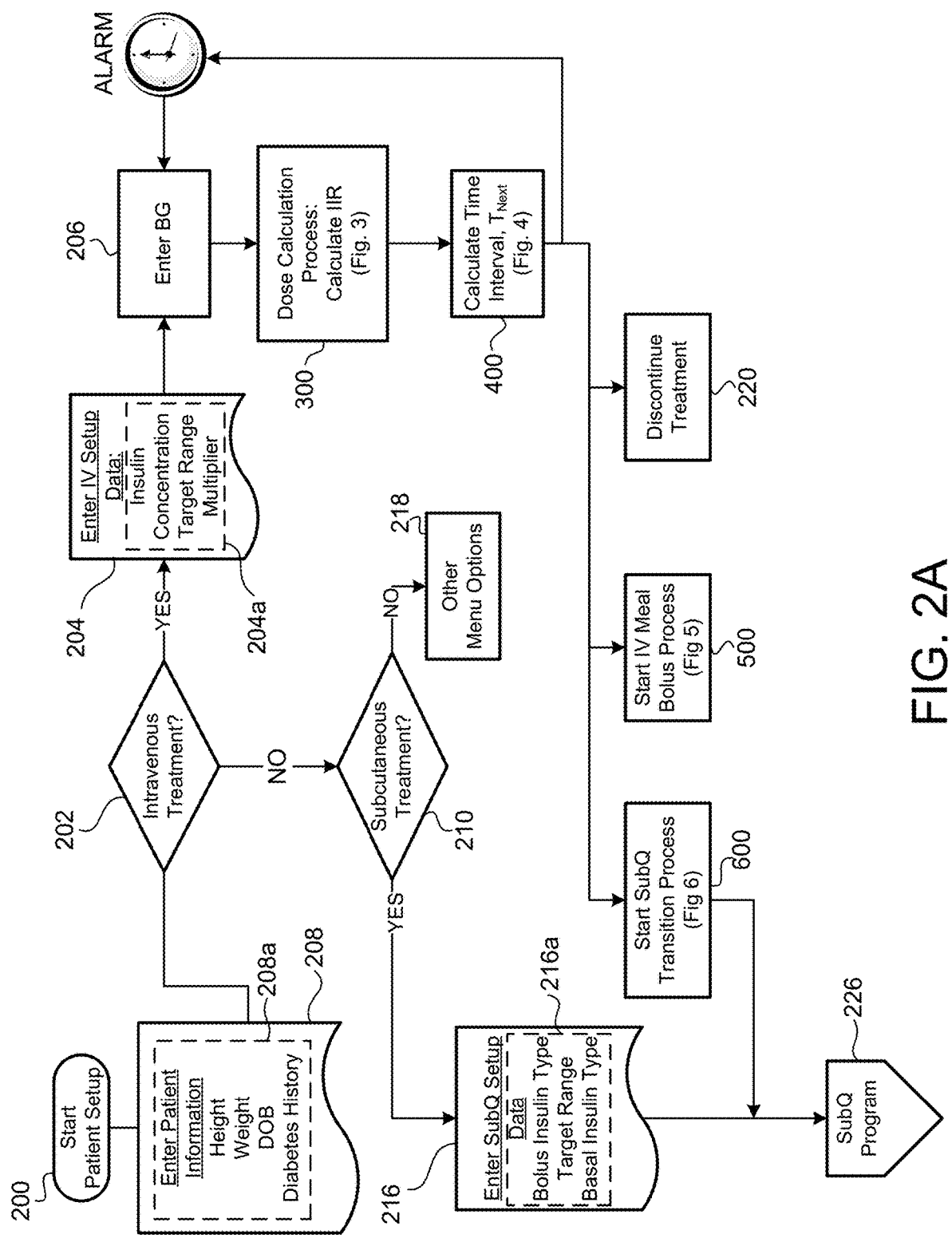
FIG. 2A is a schematic view of an exemplary process for monitoring the blood glucose level of a patient.

In some implementations, an electronic medical record system 140 is located at a hospital 42 (or a doctor's office) and includes a data processor 142, a non-transitory memory 144, and a display 146 (e.g., touch display or non-touch display). The transitory memory 144 and the display 146 are in communication with the data processor 142. In some examples, the hospital electronic medical system 140 includes a keyboard 148 in communication with the data processor 142 to allow a user 40 to input data, such as patient information 208a (FIGS. 2A and 2B). The non-transitory memory 144 maintains patient records capable of being retrieved, viewed, and, in some examples, modified and updated by authorized hospital personal on the display 146.

The dosing controller 160 is in communication with the glucometer 124 and includes a computing device 112, 132, 142 and non-transitory memory 114, 134, 144 in communication with the computing device 112, 132, 142. The dosing controller 160 executes the process 200. The dosing controller 160 stores patient related information retrieved from the glucometer 124 to determine an insulin dose rate IRR based on the received blood glucose measurement BG.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the service provider 130, and the hospital electronic medical record system 140 communicate with each other by sending and receiving signals (wired or wireless) via the network 20. In some examples, the network 20 provides access to cloud computing resources, which may be elastic/on-demand computing and/or storage resources 24 available over the network 20. The term 'cloud' services generally refers to a service performed not locally on a user's device, but rather delivered from one or more remote devices accessible via one or more networks 20.

Referring to FIGS. 1B and 2A-2C, the process 200 receives parameters (e.g., patient condition parameters) inputted via the client device 110, the service provider 130, and/or the hospital system 140, analyzes the inputted parameters, and determines a personalized dose of insulin to bring and maintain a patient's blood glucose level BG into a preferred target range $BG_{TR}$.

In some implementations, before the process 200 begins to receive the parameters, the process 200 may receive a username and a password (e.g., at a login screen displayed on the display 116, 146) to verify that a qualified and trained healthcare professional 40 is initiating the process 200 and entering the correct information that the process 200 needs to accurately administer insulin to the patient 10. The system 100 may customize the login screen to allow a user 40 to reset their password and/or username. Moreover, the system 100 may provide a logout button (not shown) that allows the user 40 to log out of the system 100. The logout button may be displayed on the display 116, 146 at any time during the execution of the process 200.

The clinical decision support system 100 may include an alarm system 120 that alerts a user 40 when the patient's blood glucose level BG is outside the target range $BG_{TR}$. The alarm system 120 may produce an audible sound via speaker 122 in the form of a beep or some like audio sounding mechanism. In some examples, the alarm system 120 displays a warning message or other type of indication on the display 116 of the patient device 110 to provide a warning message. The alarm system 120 may also send the audible and/or visual notification via the network 20 to the hospital system 140 (or any other remote station) for display on the display 146 of the hospital system 140 or played through speakers 152 of the hospital system 140.

The process 200 prompts a user 40 to input patient information 208a at block 208. The user 40 may input the patient information 208a, for example, via the user device 110 or via the hospital electronic medical record systems 140 located at a hospital 42 (or a doctor's office). The user 40 may input new patient information 208a as shown in FIG. 2B or retrieve previously stored patient information 208a as shown in FIG. 2C. In some implementations, the process 200 provides the user 40 with a patient list 209 (FIG. 2C) where the user 40 selects one of the patient names from the patient list 209, and the process 200 retrieves that patient's information 208a. The process 200 may allow the user 40 to filer the patient list 209, e.g., alphabetically (first name or last name), by location, patient identification. The process 200 may retrieve the patient information 208a from the non-transitory memory 144 of the hospital's electronic medical system 140 or the non-transitory memory 114 of the patient device 110 (e.g., where the patient information 208a was previously entered and stored). The patient information 208a may include, but is not limited to, a patient's name, a patient's identification number (ID), a patient's height, weight, date of birth, diabetes history, physician name, emergency contact, hospital unit, diagnosis, gender, room number, and any other relevant information. In some examples, the diagnosis may include, but is not limited to, burn patients, Coronary artery bypass patients, stoke patients, diabetic ketoacidosis (DKA) patients, and trauma patients. After the user 40 completes inputting the patient information 208a, the process 200 at block 202 determines whether the patient 10 is being treated with an intravenous treatment module by prompting the user 40 (e.g., on the display 116, 146) to input whether the patient 10 will be treated with an intravenous treatment module. If the patient 10 will not be treated with the intravenous treatment module, the process 200 determines at block 210 whether the patient 10 will be treated with a subcutaneous treatment module, by asking the user 40 (e.g., by prompting the user on the display 116, 146). If the user 40 indicates that the patient 10 will be treated with the subcutaneous treatment, the process 200 flows to block 216, where the user 40 enters patient subcutaneous information 216a, such as bolus insulin type, target range, basal insulin type and frequency of distribution (e.g., 1 does per day, 2 doses per day, 3 doses per day, etc.), patient diabetes status, subcutaneous type ordered for the patient (e.g., Basal/Bolus and correction that is intended for patients on a consistent carbohydrate diet, or Basal and correction that is intended for patients who are NPO or on continuous enteral feeds), frequency of patient blood glucose measurements, or any other relevant information. In some implementations, the patient subcutaneous information 216a is prepopulated with default parameters, which may be adjusted or modified. When the user 40 enters the patient subcutaneous information 216, the subcutaneous program begins at block 226. The process may determine whether the patient 10 is being treated with an intravenous treatment or a subcutaneous treatment by prompting the user 40 to select between two options (e.g., a button displayed on the display 116, 146), one being the intravenous treatment and the other begin the subcutaneous treatment.

In some implementations and referring back to block 202, if the process 200 determines that the patient 10 will be treated with the intravenous treatment module, the process 200 prompts the user 40 at block 204 for setup data 204a, such as patient parameters 204a relevant to the intravenous treatment mode. In some examples, the patient parameter 204a relating to the intravenous treatment may be prepopulated, for example, with default values that may be adjusted and modified by the user 40. These patient parameters 204a may include an insulin concentration (i.e., the strength of insulin being used for the intravenous dosing, which may be measured in units/milliliter), the type of insulin and rate being administered to the patient, the blood glucose target range $BG_{TR}$, the patient's diabetes history, a number of carbohydrates per meal, or any other relevant information. In some implementations, the type of insulin and the rate of insulin depend on the BG of the patient 10. For example, the rate and type of insulin administered to a patient 10 when the blood glucose value BG of the patient 10 is greater or equal to 250 mgl/dl may be different than the rate and type of insulin administered to the patient 10 when the blood glucose value BG of the patient is greater than 250 ml/dl. The blood glucose target range $BG_{TR}$ may be a configurable parameter, customized based on various patient factors. The blood glucose target range $BG_{TR}$ may be limited to 40 mg/dl (e.g., 100-140 mg/dl, 140-180 mg/dl, and 120-160 mg/dl).

After the user 40 inputs patient parameters 204a for the intravenous treatment at block 204, the process 200 prompts the user 40 to input the blood glucose value BG of the patient 10 at block 206. The blood glucose value BG may be manually inputted by the user 40, sent via the network 20 from a glucometer 124, sent electronically from the hospital information or laboratory system 140, or other wireless device. The process 200 determines a personalized insulin dose rate, referred to as an insulin infusion rate IIR, using the blood glucose value BG of the patient 10 and a dose calculation process 300.

Figure 3:
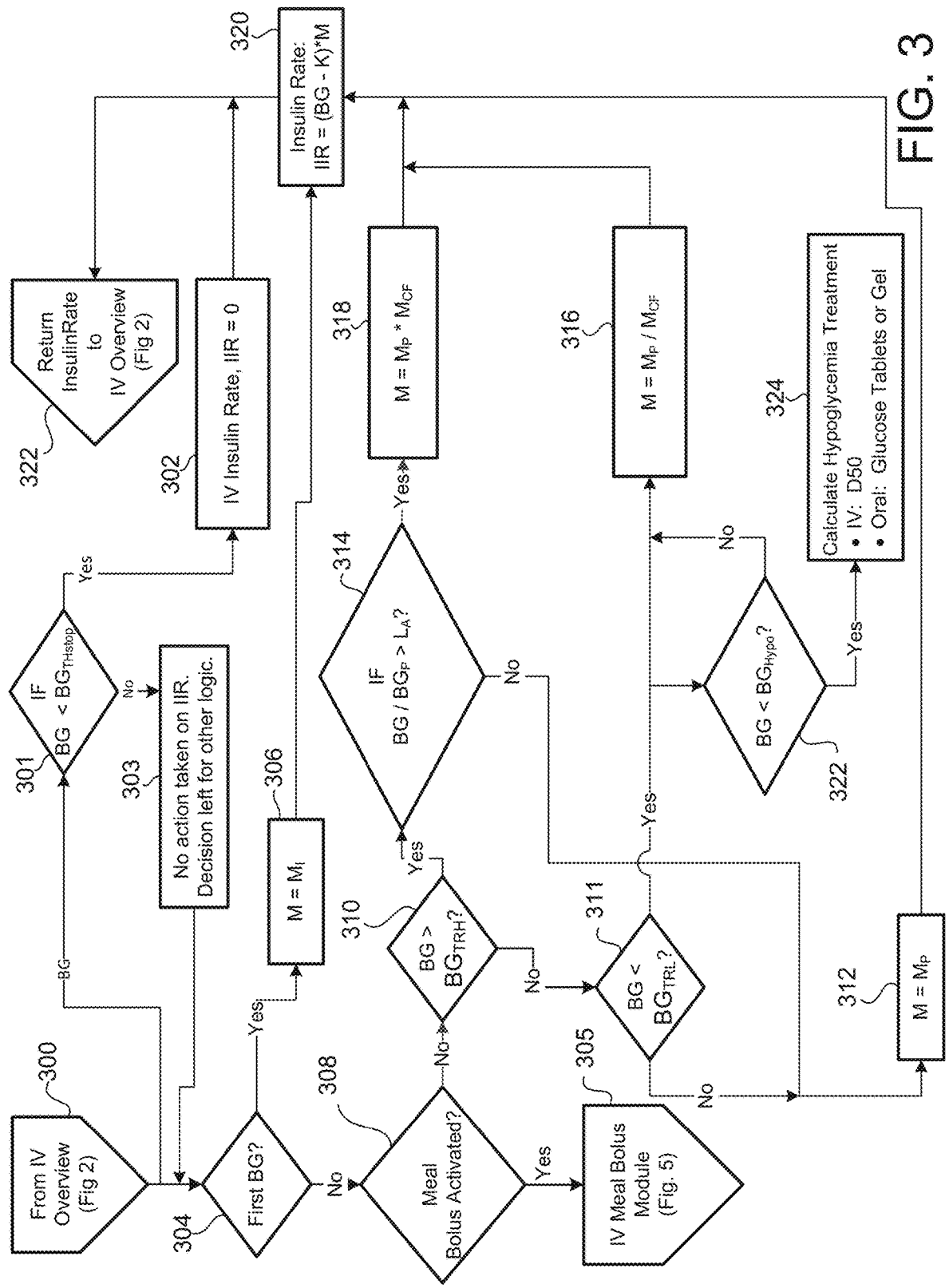
FIG. 3 is a schematic view of an exemplary dose calculation process of FIG. 2A.

FIG. 3 provides a dose calculation process 300 for calculating the insulin infusion rate IIR of the patient 10 for intravenous treatment after the process 200 receives the patient information 208a discussed above (including the patients' blood glucose value BG). At block 301 the dose calculation process 300 determines if the patient's blood glucose BG is less than a stop threshold value $BG_{THstop}$. If not, then at block 303 the dose calculation process 300 goes to block 304 without taking any action. If, however, the patient's blood glucose BG is less than a stop threshold value $BG_{THstop}$, then the calculation dose process sets the patient's regular insulin dose rate IRR to zero at block 302, which then goes to block 322. The dose calculation process 300 determines at decision block 304 if the inputted blood glucose value BG is the first inputted blood glucose value.

The patient's regular insulin dose rate IIR is calculated at block 320 in accordance with the following equation:

$$IIR=(BG-K)*M \quad (3A)$$

where K is a constant, known as the Offset Target, with the same unit of measure as blood glucose and M is a unit-less multiplier. In some examples, the Offset Target K is lower than the blood glucose target range of the patient 10. The Offset Target K allows the dose calculation process 300 to calculate a non-zero stable insulin dose rate even with a blood glucose result is in the blood glucose target range $BG_{TR}$.

The initial multiplier $M_I$, determined by the physician 40, approximates the sensitivity of a patient 10 to insulin. For example, the initial multiplier equals 0.02 for adults ages 18 and above. In some examples, the initial multiplier $M_I$ equals 0.01 for frail elderly patients 10 who may be at risk for complications arising when their blood glucose level BG falls faster than 80 mg/dl/hr. Moreover, the physician 40 may order a higher initial multiplier $M_I$ for patients 10 with special needs, such as CABG patients (i.e., patients who have undergone coronary artery bypass grafting) with BMI (Body Mass Index which is a measure for the human body shape based on the individual's mass and height) less than 30 might typically receive an initial multiplier of 0.05, whereas a patient with BMI greater than 30 might receive an initial multiplier $M_I$ of 0.06. In addition, a patient's weight may be considered in determining the value of the initial multiplier $M_I$, for examples, in pediatric treatments, the system 100 calculates a patient's initial multiplier $M_I$ using the following equation:

$$M_I=0.0002 \times \text{Weight of patient (in kilograms)} \quad (3B)$$

In some implementations, K is equal to 60 mg/dl. The dose calculation process 300 determines the target blood glucose target range $BG_{TR}$ using two limits inputted by the user 40, a lower limit of the target range $BG_{TRL}$ and an upper (high) limit of the target range $BG_{TRH}$. These limits are chosen by the user 40 so that they contain the desired blood glucose target as the midpoint. Additionally, the Offset Target K may be calculated dynamically in accordance with the following equation:

$$K=BG_{Target}-\text{Offset}, \quad (4)$$

where $BG_{Target}$ is the midpoint of the blood glucose target range $BG_{TR}$ and Offset is the preconfigured distance between the target center $BG_{Target}$ and the Offset Target, K.

In some implementations, the insulin dose rate IRR may be determined by the following process on a processor 112, 132, 142. Other processes may also be used.

```
function IIR($sf, $current_bg, $bg_default=60, $insulin_
    concentration, $ins_units_of_measure='units/hr') {
  settype($sf,'float');
  settype($bg_default,'float');
  settype($current_bg,'float');
  settype($insulin_concentration,'float');
  /*
    @param $sf=sensitivity factor from db
    @param $current_bg=the current bg value being
      submitted
    @param $db_default=the default "Stop Insulin
      When" value . . . . If it isn't passed, it defaults to
      60
    @param $insulin_concentration=the default insulin
      concentration from settings
  */
  if($current_bg>60) {
    $iir=array( );
    $iir[0]=round(($current_bg-$bg_default)*$sf, 1);
    if ($ins_units_of_measure !='units/hr'){
      $iir[1]=round(($current_bg-$bg_default)*$sf/
        $insulin_concentration,1);
    }
    return $iir;
  } else {
    return 0;
  }
}
```

Referring to decision block 304, when the dose calculation process 300 determines that the inputted blood glucose value BG is the first inputted blood glucose value, then the dose calculation process 300 defines the value of the current multiplier M equal to an initial multiplier ($M_I$) at block 306. The dose calculation process 300 then calculates, at block 320, the Insulin Infusion Rate in accordance with the BR equation (EQ. 3A) and returns to the process 200 (see FIG. 2).

However, referring back to decision block 304, when the dose calculation process 300 determines that the inputted blood glucose value BG is not the first inputted blood glucose value, the dose calculation process 300 determines if the Meal Bolus Module has been activated at decision block 308. If the dose calculation process 300 determines that the Meal Bolus Module has been activated, then the dose calculation process 300 begins a Meal Bolus process 500 (see FIG. 5).

Referring back to decision block 308, if the Meal Bolus Module has not been activated, the dose calculation process 300 determines, at decision block 310, if the current blood glucose value BG is greater than the upper limit $BG_{TRH}$ of the blood glucose target range $BG_{TR}$. If the blood glucose value BG is greater than the upper limit $BG_{TRH}$ of the blood glucose target range BG R, the dose calculation process 300 determines, at block 314, a ratio of the current blood glucose value BG to the previous blood glucose value $BG_P$, where $BG_P$ was measured at an earlier time than the current BG. The process 200 then determines if the ratio of the blood glucose to the previous blood glucose, $BG/BG_P$, is greater than a threshold value $L_A$, as shown in the following equation:

$$(BG/BG_P) > L_A \quad (5)$$

where BG is the patient's current blood glucose value; $BG_P$ is the patient's previous blood glucose value; and $L_A$ is the threshold ratio of $BG/BG_P$ for blood glucose values above the upper limit of the blood glucose target range $BG_{TRH}$. If the ratio $BG/BG_P$ exceeds the threshold ratio $L_A$, then the Multiplier M is increased. In some examples, the threshold ratio $L_A$ equals 0.85.

If the dose calculation process 300 determines that the ratio $(BG/BG_P)$ of the blood glucose value BG to the previous blood glucose value $BG_P$ is not greater than the threshold ratio $L_A$ for a blood glucose value BG above the upper limit $BG_{TRH}$ of the blood glucose target range $BG_{TR}$, then the dose calculation process 300 sets the value of the current multiplier M to equal the value of the previous multiplier $M_P$, see block 312.

$$M=M_P \quad (6)$$

Referring back to block 314, if the dose calculation process 300 determines that the ratio $(BG/BG_P)$ of the blood glucose value BG to the previous blood glucose $BG_P$ is greater than the threshold ratio $L_A$ for a blood glucose value above upper limit $BG_{TRH}$ of the blood glucose target range $BG_{TR}$, then dose calculation process 300 multiplies the value of the current multiplier M by a desired Multiplier Change Factor ($M_{CF}$) at block 318. The dose calculation process 300 then calculates the insulin infusion rate at block 320 using the IIR equation (EQ. 3A) and returns to the process 200 (see FIG. 2).

Referring back to block 310, when the dose calculation process 300 determines that the current blood glucose value BG is not greater than the upper limit $BG_{TRH}$ of the blood glucose target range $BG_{TR}$, the dose calculation process 300 then determines if the current blood glucose concentration BG is below the lower limit $BG_{TRL}$ of the blood glucose target range $BG_{TR}$ at decision block 311. If the current blood glucose value BG is below the lower limit $BG_{TRL}$, of the blood glucose target range $BG_{TR}$, the dose calculation process 300 at block 316 divides the value of the current multiplier M by the Multiplier Change Factor ($M_{CF}$), in accordance with the following equation:

$$M=M_P/M_{CF} \quad (7)$$

and calculates the current insulin infusion rate IIR using equation 3 at block 320 and returns to the process 200 (see FIG. 2).

At block 311, if the dose calculation process 300 determines that the blood glucose value BG is not below the lower limit of the blood glucose target range $BG_{TRL}$, the dose calculation process 300 sets the value of the current multiplier to be equal to the value of the previous multiplier $M_P$ at block 312 (see EQ. 6).

Referring again to FIG. 3, at block 311, if the current blood glucose value BG is below the lower limit of the target range $BG_{TRL}$, logic passes to decision block 322, where the process 300 determines if the current blood glucose concentration BG is below a hypoglycemia threshold $BG_{Hypo}$. If the current blood glucose BG is below the hypoglycemia threshold $BG_{Hypo}$, logic then passes to block 324, where the process 300 recommends hypoglycemia treatment, either by a calculation of an individualized dose of intravenous glucose or oral hypoglycemia treatment.

Referring back to FIG. 2A, after the dose calculation process 300 calculates the insulin infusion rate IIR, the process 200 proceeds to a time calculation process 400 (FIG. 4A) for calculating a time interval $T_{Next}$ until the next blood glucose measurement.

Figure 4A:
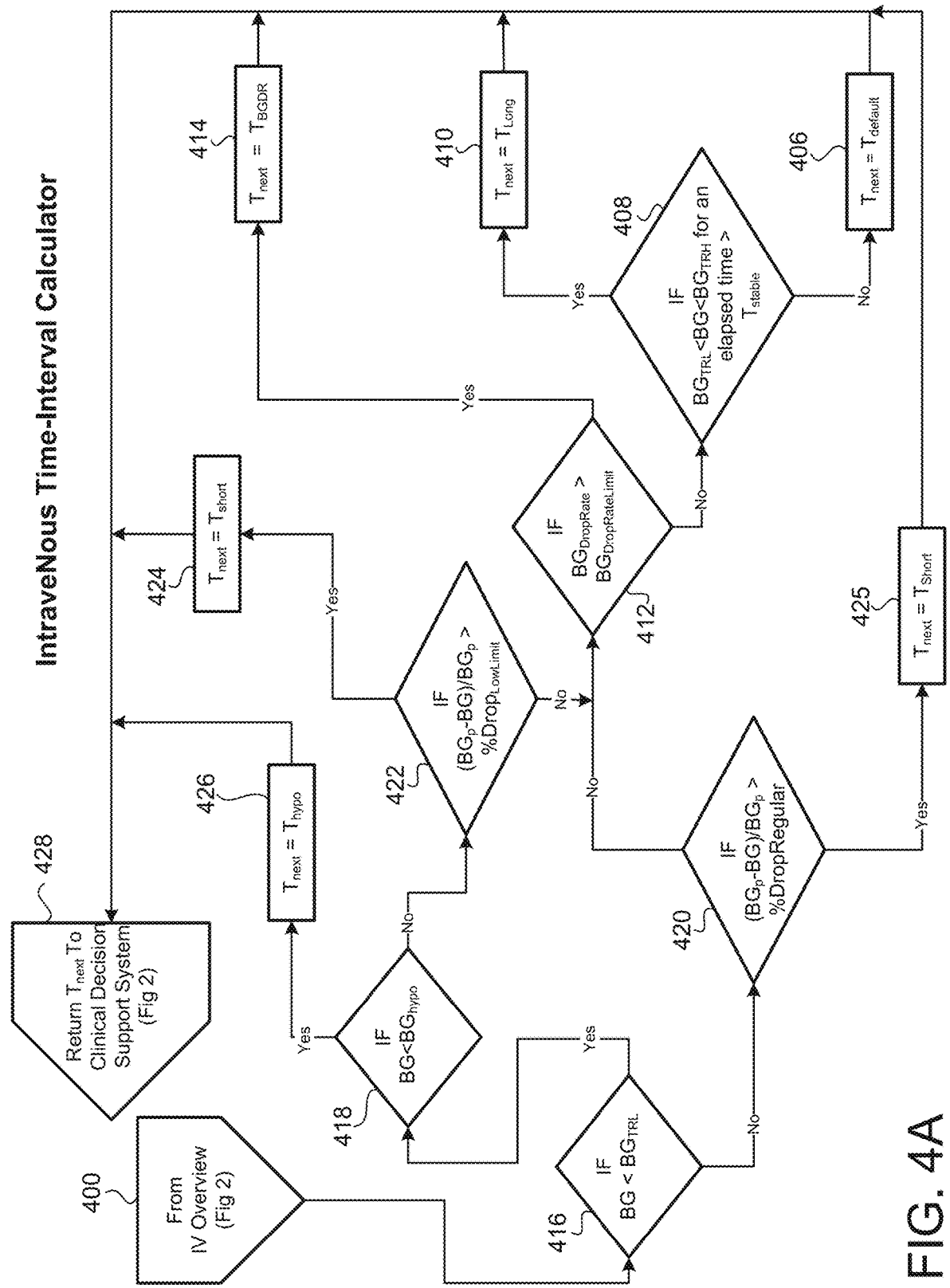
FIG. 4A is a schematic view of an exemplary calculation of the intravenous time interval of FIG. 2A.

FIG. 4A shows the time interval calculation process 400 for calculating a time interval $T_{Next}$ between the current blood glucose measurement BG and the next blood glucose measurement $BG_{next}$. The time-duration of blood glucose measurement intervals $T_{Next}$ may vary and the starting time interval can either be inputted by a user 40 at the beginning of the process 200, 300, 400, or defaulted to a predetermined time interval, $T_{Default}$ (e.g., one hour). The time interval $T_{Next}$ is shortened if the blood glucose concentration BG of the patient 10 is decreasing excessively, or it may be lengthened if the blood glucose concentration BG of the patient 10 becomes stable within the blood glucose target range $BG_{TR}$.

The time-interval calculation process 400 determines a value for the time interval $T_{Next}$ based on several conditions. The time-interval process 400 checks for the applicability of several conditions, where each condition has a value for $T_{next}$ that is triggered by a logic-test (except $T_{default}$). The process 400 selects the lowest value of $T_{next}$ from the values triggered by logic tests (not counting $T_{default}$). If no logic test was triggered, the process selects $T_{default}$. This is accomplished in FIG. 4A by the logic structure that selects the lowest values of $T_{next}$ first. However, other logic structures are possible as well.

The time calculation process 400 determines at decision block 416 if the current blood glucose BG is below the lower limit $BG_{TRL}$ (target range low limit) of the blood glucose target range $BG_{TR}$. If the current blood glucose BG is below the lower limit $BG_{TRL}$ of the blood glucose target range $BG_{TR}$, then the time calculation process 400 determines, at decision block 418, if the current blood glucose BG is less than a hypoglycemia-threshold blood glucose level $BG_{Hypo}$.

If the current blood glucose BG is less than the hypoglycemia-threshold blood glucose level $BG_{Hypo}$, the time calculation process 400 sets the time interval $T_{Next}$ to a hypoglycemia time interval $T_{Hypo}$, e.g., 15 or 30 minutes, at block 426. Then the time calculation process 400 is complete and returns to the process 200 (FIG. 2) at block 428.

If the current blood glucose BG is not less than (i.e., is greater than) the hypoglycemia-threshold blood glucose level $BG_{Hypo}$ at block 418, the time calculation process 400 determines at block 422 if the most recent glucose percent drop $BG_{\%\ Drop}$, is greater than the threshold glucose percentage drop % $Drop_{Low\ Limit}$ (for a low BG range) using the following equation:

$$BG_{\%drop} > \%Drop_{Low\ Limit} \tag{8A}$$

since $$BG_{\%drop} = \left(\frac{(BG_P - BG)}{BG_P}\right) \tag{8B}$$

then, $$\left(\frac{(BG_P - BG)}{BG_P}\right) > \%Drop_{Low\ Limit} \tag{8C}$$

where $BG_P$ is a previously measured blood glucose.

If the current glucose percent drop $BG_{\%\ Drop}$, is not greater than the limit for glucose percent drop (for the low BG range) % $Drop_{Low\ Limit}$, the time calculation process 400 passes the logic to block 412. In some examples, the low limit % $Drop_{Low\ Limit}$ equals 25%.

Referring back to block 422, if the current glucose percent drop $BG_{\%\ Drop}$ is greater than the limit for glucose percent drop (for the low BG range) % $Drop_{Low\ Limit}$, the time calculation process 400 at block 424 sets the time interval to a shortened time interval $T_{Short}$, for example 20 minutes, to accommodate for the increased drop rate of the blood glucose BG. Then the time calculation process 400 is complete and returns to the process 200 (FIG. 2) at block 428.

Referring back to decision block 416, if the time calculation process 400 determines that the current blood glucose BG is not below the lower limit $BG_{TRL}$ for the blood glucose target range $BG_{TR}$, the time calculation process 400 determines at block 420 if the blood glucose BG has decreased by a percent of the previous blood glucose that exceeds a limit % $Drop_{Regular}$ (for the regular range, i.e., blood glucose value $BG > BG_{TRL}$), using the formula:

$$\left(\frac{(BG_P - BG)}{BG_P}\right) > \%Drop_{Regular} \tag{9}$$

If the blood glucose BG has decreased by a percentage that exceeds the regular threshold glucose percent drop (for the regular BG range) % $Drop_{Regular}$, the time calculation process 400, at block 425, sets the time interval to the shortened time interval $T_{Short}$, for example 20 minutes. A reasonable value for % $Drop_{Regular}$ for many implementations is 66%. Then the time calculation process 400 is complete and returns to the process 200 (FIG. 2) at block 428. If, however, the glucose has not decreased by a percent that exceeds the threshold glucose percent drop % $Drop_{Regular}$, (for the regular BG range), the time calculation process 400 routes the logic to block 412. The process 400 determines, at block 412, a blood glucose rate of descent $BG_{DropRate}$ based on the following equation:

$$BG_{DropRate} = (BG_P - BG)/(T_{Current} - T_{Previous}) \tag{10}$$

where $BG_P$ is the previous blood glucose measurement, $T_{Current}$ is the current time and $T_{Previous}$ is the previous time. Moreover, the process 400 at block 412 determines if the blood glucose rate of descent $BG_{DropRate}$ is greater than a preconfigured drop rate limit $BG_{dropRateLimit}$.

If the time calculation process 400 at block 412 determines that the blood glucose rate of descent $BG_{DropRate}$, has exceeded the preconfigured drop rate limit $BG_{dropRateLimit}$, the time interval $T_{Next}$ until the next blood glucose measurement is shortened at block 414 to a glucose drop rate time interval $T_{BGDR}$, which is a relatively shorter time interval than the current time interval $T_{Current}$, as consideration for the fast drop. The preconfigured drop rate limit $BG_{dropRateLimit}$ may be about 100 mg/dl/hr. The glucose drop rate time interval $T_{BGDR}$ may be 30 minutes, or any other predetermined time. In some examples, a reasonable value for $T_{Default}$ is one hour. Then the time calculation process 400 is complete and returns to the process 200 (FIG. 2) at block 428.

If the time calculation process 400 determines at block 412 that the glucose drop rate $BG_{DropRate}$ does not exceed the preconfigured rate limit $BG_{dropRateLimit}$, the time calculation process 400 determines, at block 408, if the patient's blood glucose concentration BG has been within the desired target range $BG_{TR}$ (e.g., $BG_{TRL} < BG < BG_{TRH}$) for a period of time $T_{Stable}$. The criterion for stability in the blood glucose target range $BG_{TR}$ is a specified time in the target range $BG_{TR}$ or a specified number of consecutive blood glucose measurements in the target range $BG_{TR}$. For example, the stable period of time $T_{Stable}$ may be one hour, two hours, two and a half hours, or up to 4 hours. If the stability criterion is met then the time interval $T_{Next}$ until the next scheduled blood glucose measurement BG may be set at block 410 to a lengthened time interval $T_{Long}$ (such as 2 hours) that is generally greater than the default time interval $T_{Default}$. Then the time calculation process 400 is complete and returns to the process 200 (FIG. 2) at block 428. If the time calculation process 400 determines that the patient 10 has not met the criteria for stability, the time calculation process 400 sets the time interval $T_{Next}$ to a default time interval $T_{Default}$ at block 406. Then the time calculation process 400 is complete and returns to the process 200 (FIG. 2) at block 428.

Referring to FIGS. 4B and 4C, once the time calculation process 400 calculates the recommended time interval $T_{Next}$, the process 200 provides a countdown timer 430 that alerts the user 40 when the next blood glucose measurement is due. The countdown timer 430 may be on the display 116 of the patient device 110 or displayed on the display 146 of the hospital system 140. When the timer 430 is complete, a "BG Due!" message might be displayed as shown in FIG. 4B. The countdown timer 430 may include an overdue time 432 indicating the time late if a blood glucose value is not entered as scheduled.

In some implementations, the countdown timer 430 connects to the alarm system 120 of the user device 110. The alarm system 120 may produce an audible sound via the speaker 122 in the form of a beep or some like audio sounding mechanism. The audible and/or visual notification may also be sent via the network to the hospital system 140 (or any other remote station) and displayed on the display 146 of the hospital system 140 or played through speakers 152 of the hospital system 140, or routed to the cell phone or pager of the user. In some examples, the audible alarm using the speakers 122 is turned off by a user selection 434 on the display 116 or it is silenced for a preconfigured time. The display 116, 143 may show information 230 that includes the patient's intravenous treatment information 230a or to the patient's subcutaneous treatment information 230b. In some examples, the user 40 selects the countdown timer 430 when the timer 430 indicates that the patient 10 is due for his or her blood glucose measurement. When the user 40 selects the timer 430, the display 116, 146 allows the user 40 to enter the current blood glucose value BG as shown in FIG. 4D. For intravenous patients 10, the process 200 may ask the user 40 (via the display 116, 146) if the blood glucose is pre-meal blood glucose measurement (as shown in FIG. 4D). When the user 40 enters the information 230 (FIG. 4D), the user 40 selects a continue button to confirm the entered information 230, which leads to the display 116, 146 displaying blood glucose information 230c and a timer 430 showing when the next blood glucose measurement BG is due (FIG. 4E). In addition, the user 40 may enter the patient's blood glucose measurement BG at any time before the timer 430 expires, if the user 40 selects the 'enter BG' button 436. Therefore, the user 40 may input blood glucose values BG at any time, or the user 40 may choose to start the Meal Bolus module process 500 (see FIG. 5) by selecting the start meal button 438 (FIG. 4E), transition the patient to SubQ insulin therapy 600 (see FIG. 6), or discontinue treatment 220.

Figure 5A:
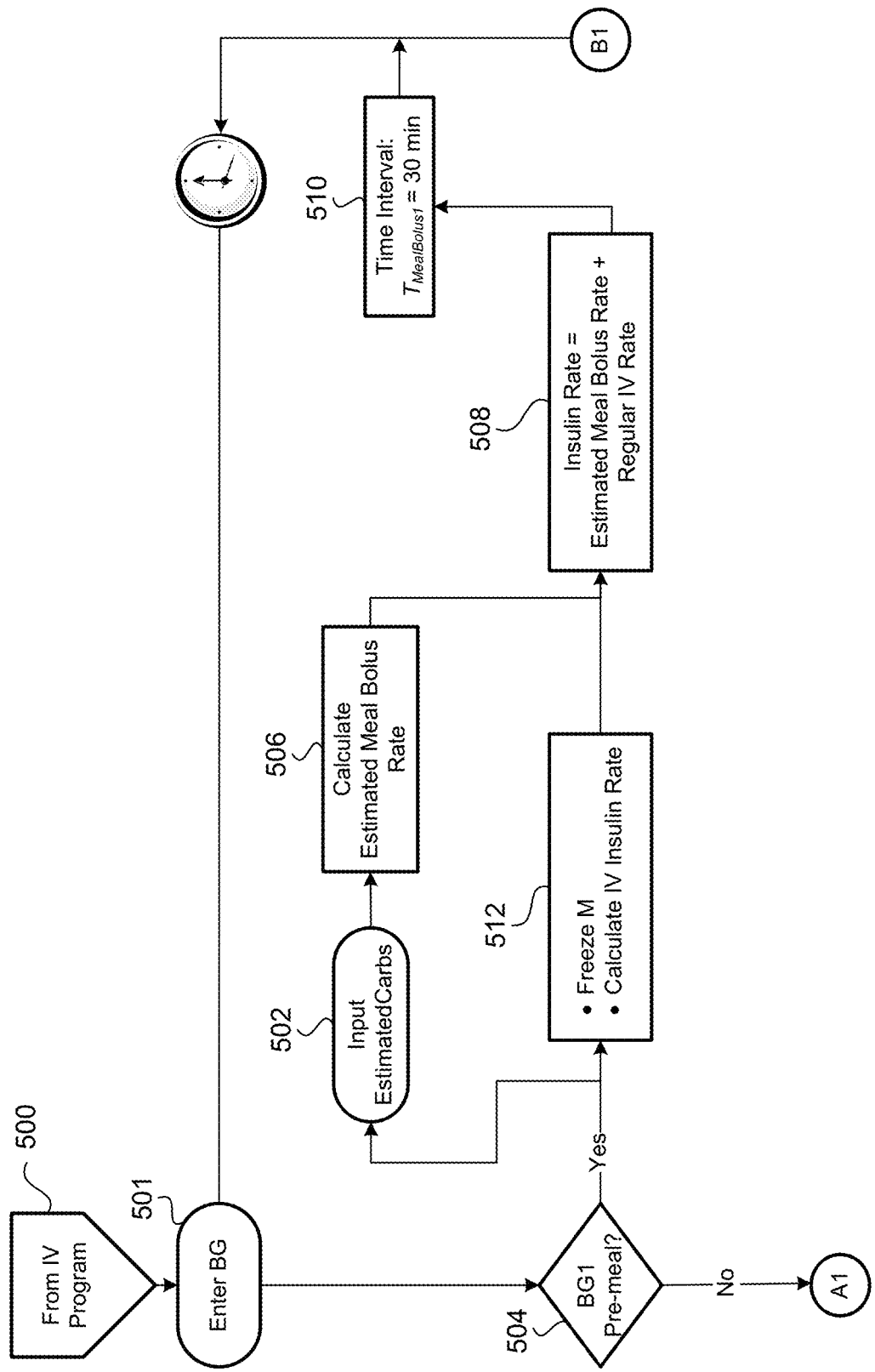
FIGS. 5A and 5B are schematic views of an exemplary meal bolus process of FIG. 2A.
Figure 5B:
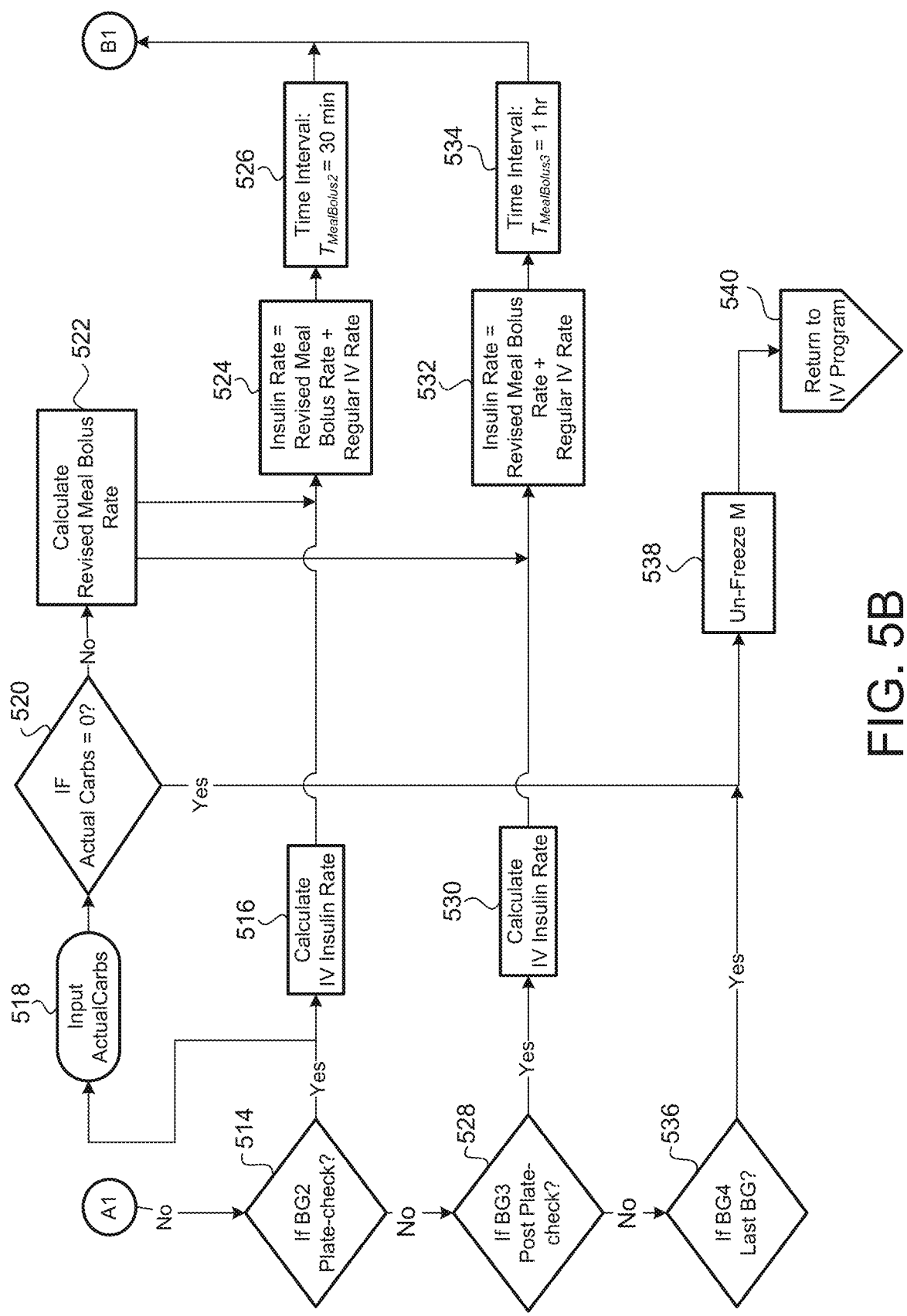

Referring to FIGS. 5A-5F, in some implementations, the process 200 includes a process where the patient's blood glucose level BG is measured prior to the consumption of caloric intake and calculates the recommended intravenous mealtime insulin requirement necessary to control the patient's expected rise in blood glucose levels during the prandial period. When a user 40 chooses to start the Meal Bolus process 500 (e.g., when the user 40 positively answers that this is a pre-meal blood glucose measurement in FIG. 4D, or when the user 40 selects the start meal button 438 in FIG. 4E), the Meal Bolus process 500, at decision block 504, requests the blood glucose BG of the patient 10 (as shown in FIG. 5C). The user 40 enters the blood glucose value BG at 501 or the system 100 receives the blood glucose BG from a glucometer 124. This blood glucose measurement is referred to herein as the Pre-Meal BG or BG1. In some examples, where the user 40 enters the information, the user 40 selects a continue button to confirm the entered information 230c. In some examples, the intravenous meal bolus process 500 is administered to a patient 10 over a total period of time $T_{MealBolus}$. The total period of time $T_{MealBolus}$ is divided into multiple time intervals $T_{MealBolus1}$ to $T_{MealBolusN}$, where N is any integer greater than zero. In some examples, a first time interval $T_{MealBolus1}$ runs from a Pre-Meal blood glucose value BG1 at measured at time $T_1$, to a second blood glucose value BG2 at measured at time $T_2$. A second time interval $T_{MealBolus2}$ runs from the second blood glucose value BG2 measured at time $T_2$ to the third blood glucose value BG3 measured at time $T_3$. A third time interval $T_{MealBolus3}$ runs from the third blood glucose value BG3 measured at time $T_3$ to a fourth blood glucose value BG4 measured at time $T_4$. In some implementations where the time intervals $T_{MealBolusN}$ are smaller than $T_{Default}$, the user 40 should closely monitor and control over changes in the blood glucose of the patient 10. For example, a total period of time $T_{MealBolus}$ equals 2 hours, and may be comprised of: $T_{MealBolus1}$=30 minutes, $T_{MealBolus2}$=30 minutes, and $T_{MealBolus3}$=1 hour. This example ends on the fourth blood glucose measurement. When the Meal Bolus process 500 has been activated, an indication 440 is displayed on the display 116, 146 informing the user 40 that the process 500 is in progress. The Meal Bolus process 500 prompts the user 40 if the entered blood glucose value BG is the first blood glucose value prior to the meal by displaying a question on the patient display 116. If the Meal Bolus process 500 determines that the entered blood glucose value BG is the first blood glucose value (BG1) prior to the meal, then the Meal Bolus process 500 freezes the current multiplier M from being adjusted and calculates a regular intravenous insulin rate IRR at block 512. The regular intravenous insulin rate IRR may be determined using EQ. 3A. Meanwhile, at block 502, the Meal Bolus process 500 loads preconfigured meal parameters, such as meal times, insulin type, default number of carbohydrates per meal, the total period of time of the meal bolus process $T_{MealBolus}$, interval lengths (e.g., $T_{MealBolus1}$, $T_{MealBolus1}$ ... $T_{MealBolusN}$), and the percent, "C", of the estimated meal bolus to be delivered in the first interval $T_{MealBolus1}$. In some examples, when the system 100 includes a hospital electronic medical record system 140, nutritional information and number of grams of carbohydrates are retrieved from the hospital electronic medical record systems 140 automatically. The Meal Bolus process 500 allows the user 40 to select whether to input a number of carbohydrates from a selection of standard meals (AcutalCarbs) or to use a custom input to input an estimated number of carbohydrates (EstimatedCarbs) that the patient 10 is likely to consume. The Meal Bolus process 500 then flows to block 506, where the estimated meal bolus rate for the meal is calculated. The calculation process in block 506 is explained in two steps. The first step is calculation of a meal bolus (in units of insulin) in accordance with the following equation:

$$\text{Estimated Meal Bolus} = \text{EstimatedCarbs}/\text{CIR} \quad (11\text{A})$$

where CIR is the Carbohydrate-to-Insulin Ratio, previously discussed.

The Meal Bolus process 500 then determines the Estimated Meal Bolus Rate based on the following equation:

$$\text{Estimated Meal Bolus Rate} = \text{Estimated Meal Bolus} * C/T_{MealBolus1} \quad (11\text{B})$$

Where, $T_{MealBolus1}$ is the time duration of the first time interval of the Meal Bolus total period of time $T_{MealBolus}$. C is a constant adjusted to infuse the optimum portion of the Estimated Meal Bolus during first time interval $T_{MealBolus1}$.

For instance: if Estimated Meal Bolus=6 units, $T_{MealBolus1}$=0.5 hours, and C=25%, then applying Eq. 11A as an example:

Estimated Meal Bolus Rate=(6 units)*25%/(0.5 hours)=3 units/hour (11C)

The Meal Bolus process 500 calculates the Total Insulin Rate at block 508 as follows:

Total Insulin Infusion Rate=Estimated Meal Bolus Rate+Regular Intravenous Rate (12)

The Meal Bolus process 500 flows to block 510 where it sets the time interval for the first interval $T_{MealBolus1}$ to its configured value, (e.g., usually 30 minutes), which will end at the second meal bolus blood glucose (BG2).

After the first time interval $T_{MealBolus1}$ expires (e.g., after 30 minutes elapse), the Meal Bolus process 500 prompts the user 40 to enter the blood glucose value BG once again at block 501. When the Meal Bolus process 500 determines that the entered blood glucose value BG is not the first blood glucose value BG1 entered at block 504 (i.e., the pre-meal BG, BG1, as previously discussed), the process 500 flows to block 514. At block 514, the Meal Bolus process 500 determines if the blood glucose value BG is the second value BG2 entered by the user 40. If the user 40 confirms that the entered blood glucose value BG is the second blood glucose value BG2 entered, the Meal Bolus process 500 uses the just-entered blood glucose BG2 to calculate the intravenous insulin rate IRR at block 516 and flows to block 524. Simultaneously, if the blood glucose is the second blood glucose BG2, the Meal Bolus process 500 prompts the user 40 to enter the actual amount of carbohydrates that the patient 10 received at block 518. The Meal Bolus process 500 then determines at decision block 520 and based on the inputted amount of actual carbohydrates, if the patient did not eat, i.e., if the amount of carbohydrates is zero (see FIG. 5C). If the Meal Bolus process 500 determines that the patient did not eat, the Meal Bolus process 500 then flows to block 540, where the meal bolus module process 500 is discontinued, the multiplier is no longer frozen, and the time interval $T_{Next}$ is restored to the appropriate time interval $T_{Next}$, as determined by process 400. If however, the Meal Bolus process 500 determines that the patient 10 ate, i.e., the actual carbohydrates is not zero (see FIG. 5D), then The Meal Bolus process 500 flows to block 522, where it calculates a Revised meal bolus rate according to the following equations, where the Revised Meal Bolus and then an amount of insulin (in units of insulin) are calculated:

Revised Meal Bolus=ActualCarbs/CIR (13A)

The process at block 522 then determines the amount (in units of insulin) of estimated meal bolus that has been delivered to the patient 10 so far:

Estimated Meal Bolus Delivered=Estimated Meal Bolus Rate*($T_2$-$T_1$) (13B)

where time T1 is the time of when the first blood glucose value BG1 is measured and time T2 is the time when the second blood glucose value BG2 is measured.

The process at block 522 then calculates the portion of the Revised Meal Bolus remaining to be delivered (i.e., the Meal Bolus that has not yet been delivered to the patient 10) as follows:

Revised Meal Bolus Remaining=Revised Meal Bolus-Estimated Meal Bolus Delivered (13C)

The process at block 522 then calculates the Revised Meal Bolus Rate as follows:

Revised Meal Bolus Rate=Revised Meal Bolus Remaining/Time Remaining (14A)

where Time Remaining=$T_{MealBolus}$-$T_{MealBolus1}$. Since the total time interval $T_{MealBolus}$ and the first time interval $T_{MealBolus1}$ are preconfigured values, the Time Remaining may be determined.

The Meal Bolus process 500 calculates the total insulin rate at block 524 by adding the Revised Meal Bolus Rate to the regular Intravenous Rate (IIR), based on the blood glucose value BG:

Total Insulin Rate=Revised Meal Bolus Rate+IIR (14B)

The Meal Bolus process 500 flows to block 526 where it sets the time interval $T_{Next}$ to the second interval $T_{MealBolus2}$, which will end at the third meal bolus blood glucose BG3 e.g., usually 30 minutes.

After the second interval, $T_{MealBolus2}$ expires (e.g., 30 minutes), the Meal Bolus process 500 prompts the user 40 to enter the blood glucose value BG once again at block 501. The Meal Bolus process 500 determines that the entered blood glucose value BG is not the first blood glucose value entered at block 504 (previously discussed) and flows to block 514. The Meal Bolus process 500 determines that the entered blood glucose value BG is not the second blood glucose value entered at block 514 (previously discussed) and flows to block 528. At block 528, the Meal Bolus process 500 determines if the blood glucose value BG is the third value entered. If the entered blood glucose value BG is the third blood glucose value BG entered, the Meal Bolus process 500 calculates the intravenous insulin rate IRR at block 530 and flows to block 532.

At block 532 the process determines the Total Insulin Rate by adding the newly-determined Regular Intravenous Insulin Rate (IIR) to the Revised Meal Bolus Rate, which was determined at BG2 and remains effective throughout the whole meal bolus time, $T_{mealbolus}$.

The Meal Bolus process 500 flows to block 534 where it sets the time interval $T_{Next}$ to the third interval $T_{MealBolus3}$ for the fourth meal bolus blood glucose, e.g., usually minutes. In some implementations, more than 3 intervals ($T_{MealBolus1}$, $T_{MealBolus2}$ $T_{MealBolus3}$) may be used. Additional intervals $T_{MealBolusN}$ may also be used and the process handles the additional intervals $T_{MealBolusN}$ similarly to how it handles the third time interval $T_{MealBolus3}$. As discussed in the current example, the third interval $T_{MealBolus3}$ is the last time interval, which ends with the measurement of the fourth blood glucose measurement BG4.

After the third time interval, $T_{MealBolus3}$, expires (e.g., 60 minutes), the Meal Bolus process 500 prompts the user 40 to enter the blood glucose value BG once again at block 501. The Meal Bolus process 500 determines that the entered blood glucose value BG is not the first blood glucose value entered at block 504 (previously discussed) and flows to block 514. The Meal Bolus process 500 determines that the entered blood glucose value BG is not the second blood glucose value entered at block 514 (previously discussed), nor the third blood glucose level entered at block 528 and flows to block 536. At block 536, the Meal Bolus process 500 determines that the inputted blood glucose is the fourth blood glucose value BG4. In this example, the fourth blood glucose value BG4 is the last one. The process 500 then flows to block 538 where the multiplier is no longer frozen, and the time interval $T_{Next}$ is restored to the appropriate time interval $T_{Next}$, as determined by the Timer Adjustment process 400 (FIG. 4A). At this time, the Meal Bolus process 500 ends and the user 40 is prompted with a message indicating that the Meal Bolus process 500 is no longer active.

As shown in FIG. 5D, and previously discussed with respect to FIGS. 4B-4E, the process 200 provides a countdown timer 430 that alerts the user 40 when the next blood glucose measurement is due. The countdown timer 430 may be on the display 116 of the patient device 110 or displayed on the display 146 of the hospital system 140.

When the timer 430 is complete, a "BG Due!" message might be displayed as shown in FIG. 4B. Moreover, the timer 430 may be a countdown timer or a meal timer indicating a sequence of mealtime intervals (e.g., breakfast, lunch, dinner, bedtime, mid-sleep).

In some implementations, a Meal Bolus process 500 may be implemented by the following process on a processor 112, 132, 142. Other processes may also be used.

```
function PreMealIIR($PatientID, $CurrentBG, $Multi-
    plier, $InsulinConcentration,
    $EstCarbs, $ActualCarbs, $TimeInterval, $Insuli-
        nUnitsOfMeasure, $MealBolusCount){
$iir=array( );
$CarbInsulinRatio=CIR($PatientID);
$NormalInsulin=($CurrentBG-60)*$Multiplier;
if($MealBolusCount==0)
{
    //first run—Premeal Bolus
    $MealBolus=($EstCarbs/$CarbInsulinRatio);
    if($MealBolus<0)
    {$MealBolus=0;}
    $iir[0]=$NormalInsulin+($MealBolus*0.5);
    $iir[2]=($MealBolus*0.5);
    /*
    print "Premeal: MX:". $Multiplier. "<BR>";
    print ($CurrentBG-60)*$Multiplier;
    print "+";
    print ($MealBolus*0.5);
    */
} else if($MealBolusCount==1){
    //second run Post Meal Bolus
    //third run time interval coming in is actually the
    //difference between the premeal BG and the first
        Post Meal BG (second run)
    $MealBolus=($ActualCarbs/$CarbInsulinRatio);
    $OldMealBolus=($EstCarbs/$CarbInsulinRatio);
    $CurrentMealBolus=($MealBolus—
        ($OldMealBolus*0.5*$TimeInterval))/1.5;
    if($CurrentMealBolus<0)
    {$CurrentMealBolus=0;}
    $iir[0]=$NormalInsulin+$CurrentMealBolus;
    $iir[2]=$CurrentMealBolus;
    /*
    print "PlateCheck:    <BR>MX:".   $Multiplier.
        "<BR>";
    print "Est Carbs:". $EstCarbs. "<BR>";
    print "ActualCarbs:". $ActualCarbs. "<BR>";
    print    "CarbInsulinRatio:".    $CarbInsulinRatio.
        "<BR>";
    print "TimeInterval:". $TimeInterval. "<BR>";
    print "Multiplier:". $Multiplier;
    */
}
else
{
    $MealBolus=($ActualCarbs/$CarbInsulinRatio);
    $OldMealBolus=($EstCarbs/$CarbInsulinRatio);
    /*
        print "Actual Carbs:". $ActualCarbs. "<BR>";
    print "Est Carbs:". $EstCarbs. "<BR>";
    print "CIR:". $CarbInsulinRatio. "<BR>";
    print "Multiplier:". $Multiplier. "<BR>";
    print "CurrentBG:". $CurrentBG. "<BR>";
    print    "IIR:".    (($CurrentBG-60)*$Multiplier).
        "<BR>";
    print "MealBolus:". $MealBolus. "<BR>";
    print "OldMealBolus:". $OldMealBolus. "<BR>";
    print "TimeInterval:". $TimeInterval. "<BR>";
    */
    $CurrentMealBolus=($MealBolus—
        ($OldMealBolus*0.5*$TimeInterval))/1.5;
    if($CurrentMealBolus<0)
    {$CurrentMealBolus=0;{
    $iir[0]=$NormalInsulin+$CurrentMealBolus;
    $iir[2]=$CurrentMealBolus;
    /*
    print "Post PlateCheck: <BR>MX:". $Multiplier.
        "<BR>";
    print "IIR:";
    print ($CurrentBG-60)*$Multiplier. "<BR>";
    print "Est Carbs:". $EstCarbs. "<BR>";
    print "Acutal Carbs:". $ActualCarbs. "<BR>";
    print "Old Meal bolus:". $OldMealBolus. "<BR>";
    print "TimeInterval:". $TimeInterval. "<BR>";
    print "Meal bolus:". $MealBolus. "<BR>";
    print "Final Calc:". $iir[0];
    */
}
if ($InsulinUnitsOfMeasure !="units/hr")
{
    $iir[0]=$iir[0]/$InsulinConcentration;
}
return $iir;
}
```

Figure 6A:
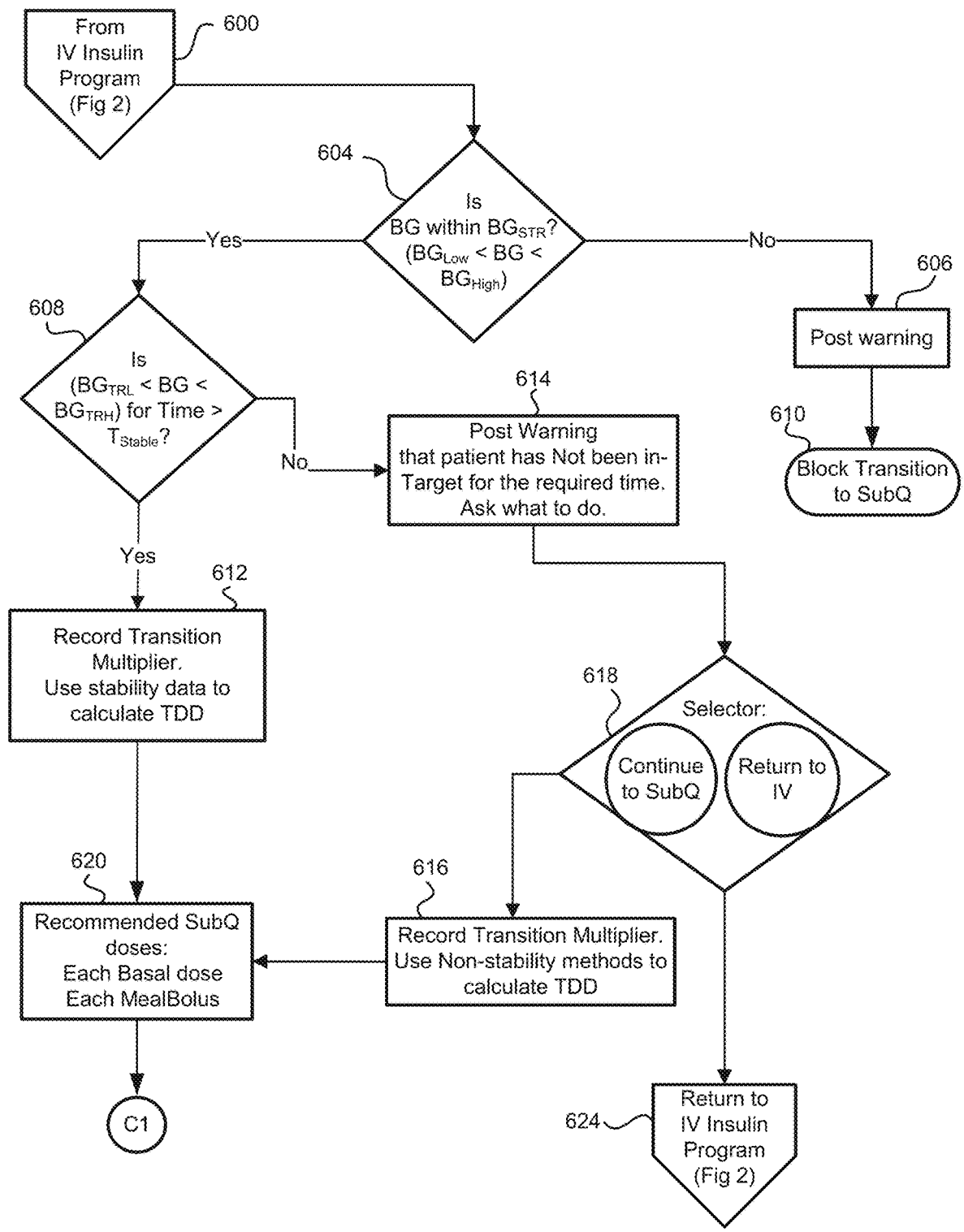
FIGS. 6A and 6B are schematic views of an exemplary subcutaneous transition process of FIG. 2A.
Figure 6B:
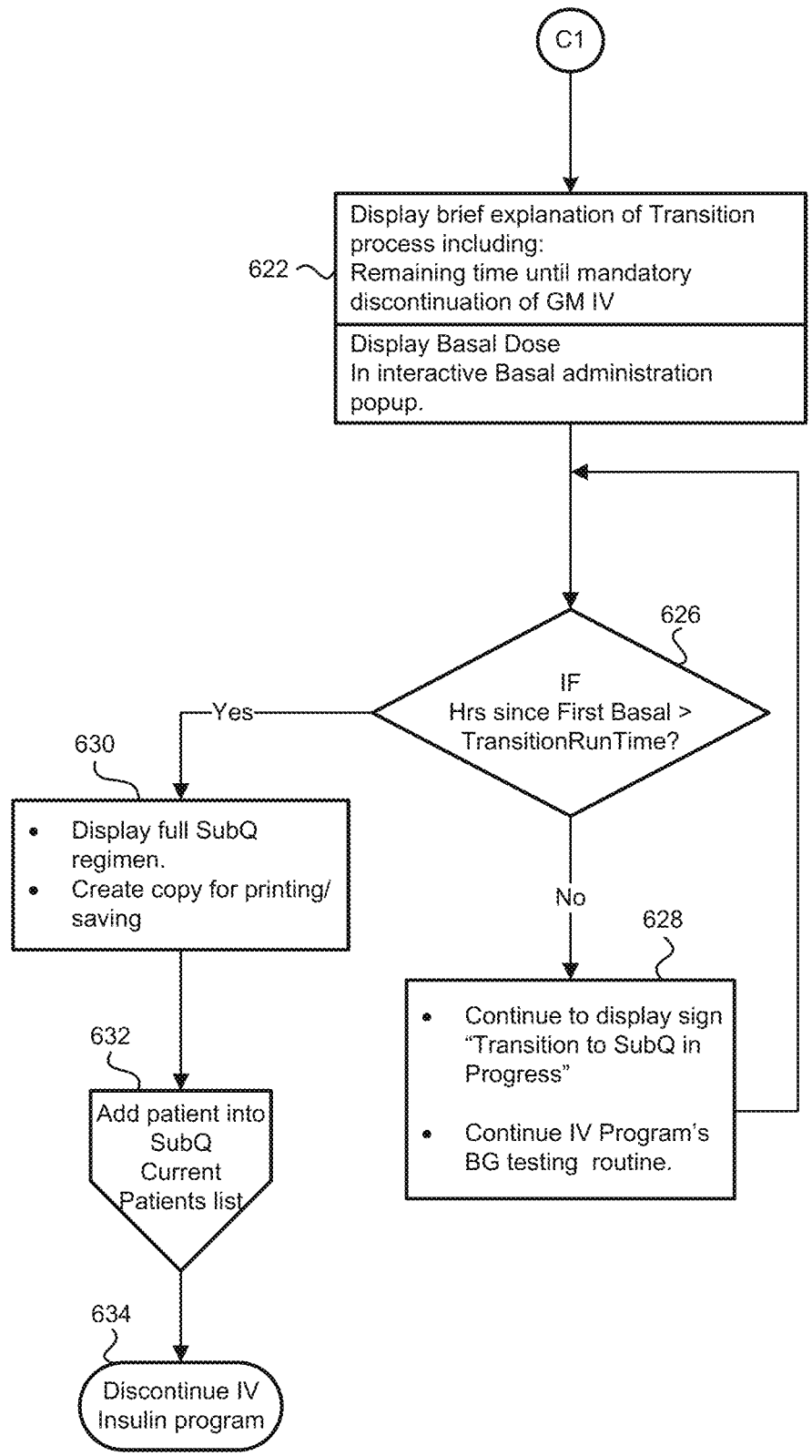
Figure 6E:
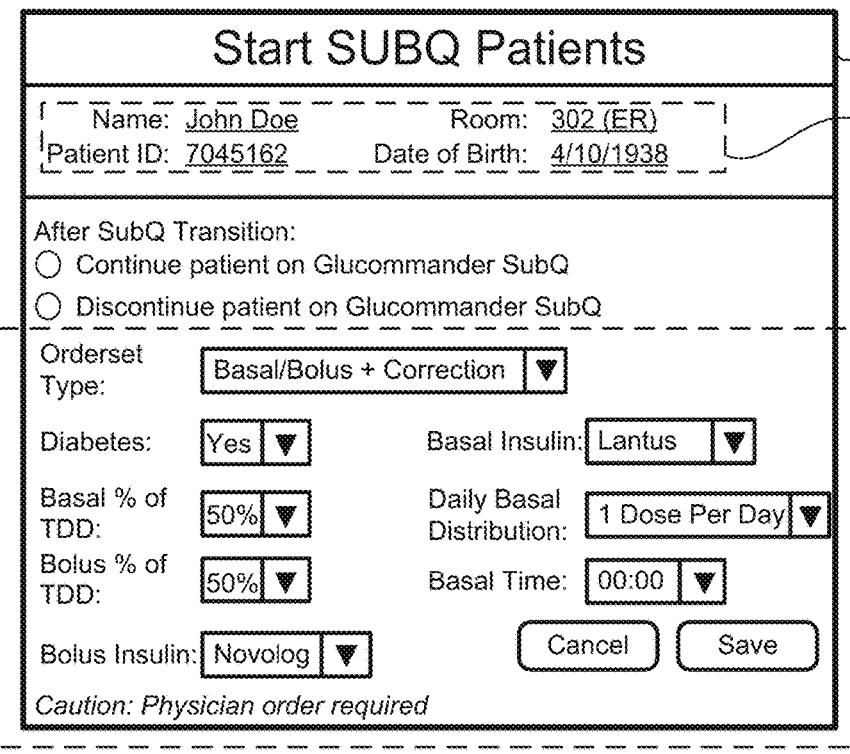
FIG. 6E is a schematic view of an exemplary display requesting information from the user relating to the patient.

Referring to FIGS. 2A and 6A, if the user elects to initiate the SubQ Transition process 600, the SubQ Transition process 600 determines at decision block 604 if the current blood glucose BG is within a preconfigured stability target range $BG_{STR}$, e.g., 70-180 mg/dl, which is usually wider than the prescribed Target Range, $BG_{TR}$. If the blood glucose BG is not within the preconfigured stability target range $BG_{STR}$ (e.g., $BG_{Low}<BG<BG_{High}$), the SubQ Transition process 600 at block 606 displays a warning notification on the patient display 116. Then, at lock 610, the SubQ Transition process 600 is automatically discontinued.

Referring back to block 604, if the blood glucose BG is within the preconfigured stability target range $BG_{STR}$ (e.g. 70-180 mg/dl), the SubQ Transition process 600 at decision block 608 determines if the patient's blood glucose measurement BG has been in the patient's personalized prescribed target range $BG_{TR}$ for the recommended stability period $T_{Stable}$, e.g., 4 hours. If the SubQ Transition process 600 determines that the blood glucose value BG has not been in the prescribed target range $BG_{STR}$ for the recommended stability period $T_{Stable}$, the SubQ Transition process 600 moves to block 614 where the system 100 presents the user 40 with a warning notification on the patient display 116, explaining that the patient 10 has not been in the prescribed target range for the recommended stability period (see FIG. 6C). The SubQ Transition process 600 continues to decision block 618 where it determines whether the user 40 wants the patient 10 to continue the SubQ Transition process or to discontinue the SubQ Transition process. The SubQ Transition process 600 displays on the display 116 of the patient device 110 the question to the user 40 as shown in FIG. 6D. If the user 40 chooses to discontinue the SubQ Transition process, the SubQ Transition process 600 flows to block 624, where the SubQ Transition process is discontinued.

Referring back to block 618, if the user 40 chooses to override the warning and continue the SubQ Transition process, the process 600 prompts the user 40 to enter SubQ information 617. The SubQ Transition process 600 flows to block 616, where the patient's SubQ Transition dose is calculated as a patient's total daily dose TDD. In some implementations, TDD is calculated in accordance with equation:

$$TDD = QuickTransitionConstant * M_{Trans} \quad (15A)$$

where QuickTransitionConstant is usually 1000, and $M_{Trans}$ is the patient's multiplier at the time of initiation of the SubQ transition process.

Referring again to block 616, in some implementations TDD is calculated by a statistical correlation of TDD as a function of body weight. The following equation is the correlation used:

$$TDD = 0.5 * Weight\ (kg) \quad (15B)$$

Figure 6F:
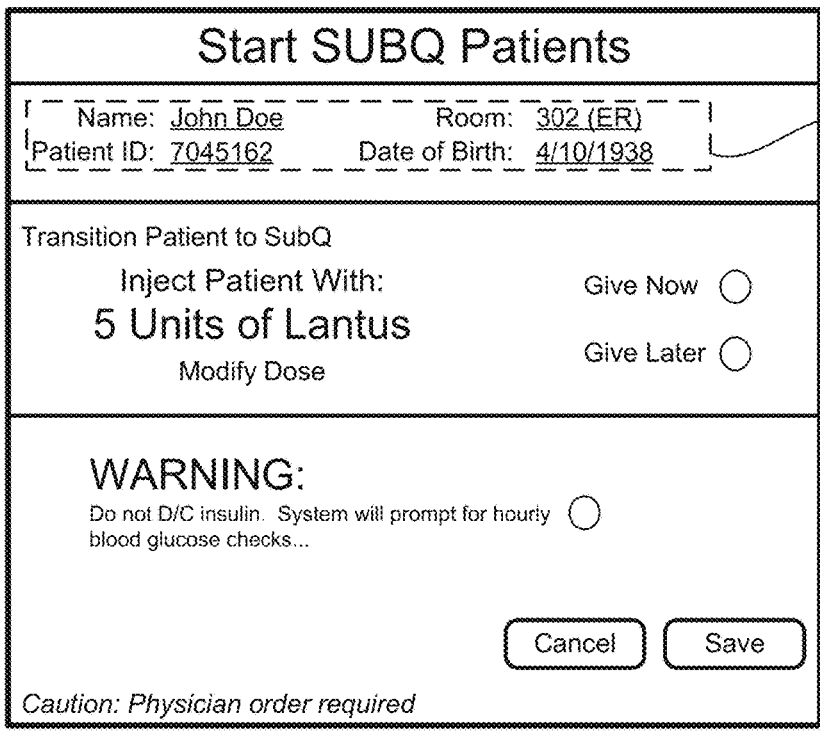
FIG. 6F is a schematic view of an exemplary display showing the recommended dose of insulin.

The SubQ Transition process 600 continues to block 620, where the recommended SubQ dose is presented to the user 40 (on the display 116) in the form of a Basal recommendation and a Meal Bolus recommendation (see FIG. 6F).

Referring again to decision block 608, if the SubQ Transition process 600 determines that the patient 10 has been in the prescribed target range $BG_{TR}$ for the recommended stability period, $T_{Stable}$, SubQ Transition process 600 continues to block 612, where the patient's total daily dose TDD is calculated in accordance with the following equation:

$$TDD = (BG_{Target} - K) * (M_{Trans}) * 24 \quad (16)$$

where $M_{Trans}$ is the patient's multiplier at the time of initiation of the SubQ transition process.

In some implementations, the patient's total daily dose TDD may be determined by the following process on a processor 112, 132, 142. Other processes may also be used.

```
function getIV_TDD($PatientID)
{
    //weight=getOneField("weight", "patients", "patientID",
        $PatientID);
    //return $weight/2;
    $CI=get instance( );
    $CI->load->model('options');
    $d=$CI->options->GetIVTDDData($PatientID);
    $TargetHigh=$d["TargetHigh"];
    $TargetLow=$d["TargetLow"];
    $Multiplier=$d["Multiplier"];
    $MidPoint=($TargetHigh+$TargetLow)/2;
    $Formula=($MidPoint-60)*$Multiplier*24;
    return $Formula;
}
```

When the patient's total daily dose TDD is calculated, the SubQ Transition process 600 continues to block 620 where the recommended SubQ dose is presented to the user 40 as described above. The SubQ Transition process 600 continues to block 622, where the SubQ Transition process 600 provides information to the user 40 including a recommended dose of Basal insulin. The user 40 confirms that the Basal insulin has been given to the patient 10; this starts a transitions timer using the TransitionRunTime$_{Next}$, usually 4 hours. At this point, normal calculation rules governing the IIR are still in effect, including the intravenous IIR timer (Timer Adjustment process 400), which continues to prompt for blood glucose tests at time intervals $T_{Next}$ as described previously. The SubQ Transition process 600 passes to decision block 626, which determines whether the recommended time interval TransitionRunTime has elapsed, e.g., 4 hours, after which time SubQ Transition process 600 continues to block 630, providing the user with subcutaneous insulin discharge orders and exiting the IV Insulin process in block 634.

Figure 7:
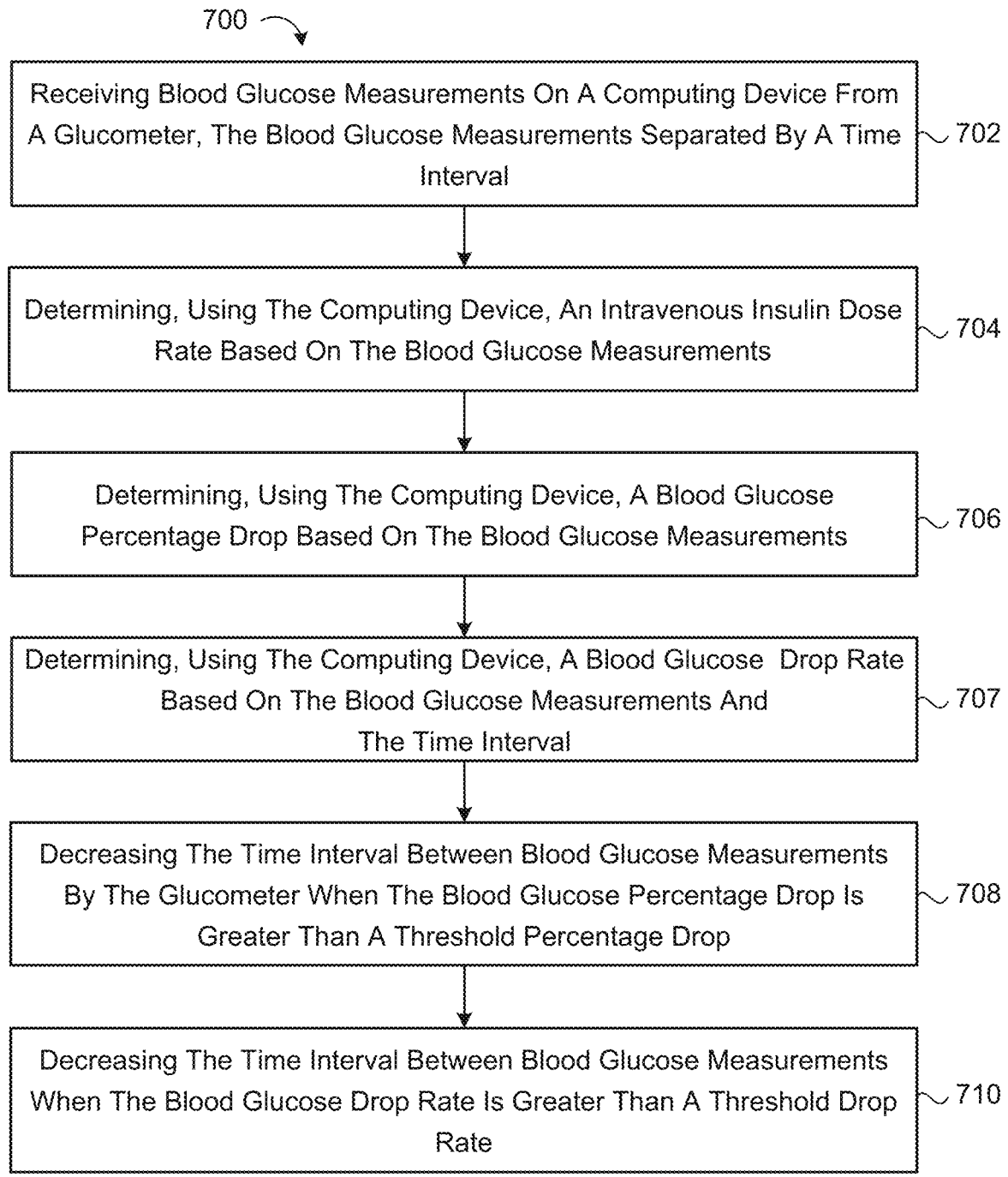
FIG. 7 is a schematic view of an exemplary arrangement of operations for administering insulin.

FIG. 7 provides an arrangement of operations for a method 700 of administering intravenous insulin to a patient 10. The method 700 includes receiving 702 blood glucose measurements BG on a computing device (e.g., a processor 112 of a patient device 110, a processor 152 of a hospital electronic medical record system 150, or a data processor 132 of a service provider 130) of a dosing controller 160 from a blood glucose measurement device 124 (e.g., glucose meter or glucometer). The blood glucose measurements BG are separated by a time interval $T_{Next}$. The method 700 includes determining 704, using the computing device 112, 132, 152, an insulin dose rate IIR based on the blood glucose measurements BG. In some implementations, the method 700 determines the insulin dose rate IRR based on a current blood glucose measurement BG, a constant K, and a multiplier M (see EQ. 3A above). The constant K may equal 60 mg/dl. The method 700 includes leaving the multiplier M unchanged between time intervals $T_{Next}$ when the current blood glucose measurement BG is greater than an upper limit $BG_{TRH}$ of the blood glucose target range $BG_{TR}$ and the blood glucose percent drop $BG_{\%\ Drop}$ from the previous blood glucose value $BG_P$ is greater than or equal to a desired percent drop BG % dropM (see EQ. 5). The method 700 also includes multiplying the multiplier M by a change factor $M_{CF}$ when the current blood glucose measurement BG is greater than an upper limit $BG_{TRH}$ of the blood glucose target range $BG_{TR}$ and the blood glucose percent drop BG % Drop (or blood glucose percent drop) is less than the desired percent drop BG % dropM. Additionally or alternatively, the method 700 includes leaving the multiplier M unchanged between time intervals $T_{Next}$ when the current blood glucose measurement BG is in the target range $BG_{TR}$ i.e. when BG is less than an upper limit $BG_{TRH}$ of the blood glucose target range and greater than the lower limit $BG_{TRL}$ of the target range, $BG_{TR}$. The method 700 also includes dividing the multiplier M by a change factor $M_{CF}$ when the current blood glucose measurement BG is less than the lower limit $BG_{TRL}$ of the blood glucose target range $BG_{TR}$. The method 700 may include setting the time interval $T_{Next}$ to a hypoglycemia time interval $T_{Hypo}$ of between about 15 minutes and about 30 minutes, when the current blood glucose measurement BG is below a hypo-threshold blood glucose level $BG_{Hypo}$.

The method 700 includes determining 706 a blood glucose drop rate $BG_{DropRate}$ based on the blood glucose measurements BG and the time interval $T_{Next}$. The method 700 includes determining 707 a blood glucose percent drop $BG_{\%\ Drop}$, using the computing device 112, 132, 152 from a previous blood glucose measurement $BG_P$. When the blood glucose drop rate $BG_{DropRate}$ is greater than a threshold drop rate $BG_{DropRateLimit}$, the method 700 includes decreasing at 708 the time interval $T_{Next}$ between blood glucose measurements measure by the glucometer.

The method 700 also includes decreasing 710 the time interval $T_{Next}$ between blood glucose measurements BG when the percent drop BG % Drop of the blood glucose BG is greater than the threshold of the percent drop % $Drop_{Regular}$, where the threshold of the percent drop % $Drop_{Regular}$ depends on whether the current blood glucose measurement BG is below a lower limit $BG_{TRL}$ of a blood glucose target range $BG_{TR}$. In some implementations, the method 700 includes decreasing the time interval $T_{Next}$ when the current blood glucose measurement BG is greater than or equal to the lower limit $BG_{TRL}$ of the blood glucose target range $BG_{TR}$ and the blood glucose percent drop BG % Drop exceeds a threshold percent drop % $Drop_{Regular}$. In some implementations, the method 700 includes decreasing the time interval $T_{Next}$ when the current blood glucose measurement BG is below the lower limit $BG_{TRL}$ of the blood glucose target range $BG_{TR}$ and above the hypo-threshold blood glucose level $BG_{Hypo}$, and the blood glucose percent drop $BG_{\% Drop}$ is greater than or equal to a threshold percent drop % $Drop_{LowLimit}$.

In some examples, the method 700 includes leaving the multiplier M unchanged for at least two subsequent time intervals, $T_{Next}$, when the current blood glucose measurement BG is a pre-meal measurement. In some examples, the method 700 includes receiving, on the computing device 112, 132, 142, a number of carbohydrates for a meal as well as a blood glucose measurement, and determining, using the computing device 112, 132, 142, an intravenous insulin rate IIR based on the blood glucose (this IIR may be calculated using EQ. 3A). In addition, the method 700 includes determining, using the computing device 112, 132, 142, a meal bolus insulin rate IIR based on the number of carbohydrates. The method 700 then calculates a Total insulin rate as the sum of the meal bolus rate and the regular intravenous rate as shown in EQ. 12. The method 700 may further include setting the time interval $T_{Next}$ to about 30 minutes. If the blood glucose measurement BG is a second consecutive measurement after (but not including) an initial pre-meal blood glucose measurement BG, the method 700 includes setting the time interval $T_{Next}$ to about 30 minutes.

In some implementations, the method 700 includes electronically displaying on a display 116, 146 a warning and blocking transition to a subcutaneous administration of insulin when the current blood glucose measurement BG is outside a stability target range $BG_{STR}$. In addition, the method 700 includes electronically displaying on the display 116, 146 a warning when the current blood glucose measurement BG is within the patient's personalized target range $BG_{TR}$ for less than a threshold stability period of time $T_{Stable}$. In some examples, the method 700 includes determining a total daily dose of insulin TDD based on the multiplier M when the current blood glucose measurement BG is within a stability target range $BG_{STR}$ for a threshold stability period of time $T_{Stable}$.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A computer-implemented method that when executed on data processing hardware causes the data processing hardware to perform operations comprising:
   receiving sequential glucose measurements of a patient, the sequential glucose measurements comprising a current glucose measurement measured at a current time;
   receiving a number of estimated grams of carbohydrates for a meal;
   determining an estimated meal bolus insulin administration rate based on the number of estimated grams of carbohydrates and a carbohydrate-insulin-ratio;
   determining a total insulin administration rate based on the current glucose measurement and the estimated meal bolus insulin administration rate; and
   transmitting the total insulin administration rate to an insulin administration device in communication with the data processing hardware, the total insulin administration rate when received by the insulin administration device, causing the insulin administration device to administer insulin to the patient at the total insulin administration rate.

2. The computer-implemented method of claim 1, wherein receiving the sequential glucose measurements comprises receiving the sequential glucose measurements from an electronic medical record (EMR) system in communication with the data processing hardware.

3. The computer-implemented method of claim 1, wherein each of the sequential glucose measurements are measured by a continuous glucose monitoring system.

4. The computer-implemented method of claim 1, wherein the operations further comprise:
   determining an intravenous insulin infusion rate based on the current glucose measurement, a constant K, and a multiplier M,
   wherein determining the total insulin administration rate comprises determining the total insulin administration rate as a sum of the intravenous insulin infusion rate and the estimated meal bolus insulin administration rate.

5. The computer-implemented method of claim 4, wherein K is equal to 60.

6. The computer-implemented method of claim 1, wherein the operations further comprise:
   determining an estimated meal bolus in units of insulin based on the number of estimated grams of carbohydrates and the carbohydrate-insulin-ratio,
   wherein determining the estimated meal bolus insulin administration rate is based on the estimated meal bolus, a delivery time duration, and a configurable constant.

7. The computer-implemented method of claim 1, wherein the operations further comprise:
   dividing a total meal time into meal time sub-intervals, a first meal time sub-interval starting with a pre-meal glucose measurement before receiving the number of estimated grams of carbohydrates; and
   determining a sub-interval total insulin administration rate for each meal time sub-interval in succession.

8. The computer-implemented method of claim 7, wherein the operations further comprise:
   receiving a number of actual grams of carbohydrates for the meal during a subsequent meal time sub-interval after the first meal time sub-interval;
   determining an actual meal bolus based on the number of actual grams of carbohydrates;
   determining an estimated delivered meal bolus insulin administration rate by multiplying the estimated meal bolus insulin administration rate by an elapsed delivery time duration;
   determining a remaining meal bolus in units of insulin by subtracting a product of the estimated delivered meal bolus insulin administration rate and an actual delivery time period from the actual meal bolus;
   determining a revised meal bolus insulin administration rate as the remaining meal bolus divided by a remaining time period duration remaining in the total meal time; and
   determining a revised total insulin administration rate as a sum of an intravenous insulin infusion rate and the revised meal bolus insulin administration rate.

9. The computer-implemented method of claim 8, wherein the operations further comprise transmitting the revised total insulin administration rate to the insulin administration device, the revised total insulin administration rate when received by the insulin administration device, causing the insulin administration device to administer insulin to the patient at the revised total insulin administration rate.

10. The computer-implemented method of claim 1, wherein the operations further comprise displaying, in a graphical user interface displayed on a screen in communication with the data processing hardware, the total insulin administration rate.

11. A system comprising:
    data processing hardware; and
    memory hardware in communication with the data processing hardware and storing instructions that when executed on the data processing hardware causes the data processing hardware to perform operations comprising:
        receiving sequential glucose measurements of a patient, the sequential glucose measurements comprising a current glucose measurement measured at a current time;
        receiving a number of estimated grams of carbohydrates for a meal;
        determining an estimated meal bolus insulin administration rate based on the number of estimated grams of carbohydrates and a carbohydrate-insulin-ratio;
        determining a total insulin administration rate based on the current glucose measurement and the estimated meal bolus insulin administration rate; and
        transmitting the total insulin administration rate to an insulin administration device in communication with the data processing hardware, the total insulin administration rate when received by the insulin administration device, causing the insulin administration device to administer insulin to the patient the total insulin administration rate.

12. The system of claim 11, wherein receiving the sequential glucose measurements comprises receiving the sequential glucose measurements from an electronic medical record (EMR) system in communication with the data processing hardware.

13. The system of claim 11, wherein each of the sequential glucose measurements are measured by a continuous glucose monitoring system.

14. The system of claim 11, wherein the operations further comprise:
    determining an intravenous insulin infusion rate based on the current glucose measurement, a constant K, and a multiplier M,
    wherein determining the total insulin administration rate comprises determining the total insulin administration rate as a sum of the intravenous insulin infusion rate and the estimated meal bolus insulin administration rate.

15. The system of claim 14, wherein K is equal to 60.

16. The system of claim 11, wherein the operations further comprise:
    determining an estimated meal bolus in units of insulin based on the number of estimated grams of carbohydrates and the carbohydrate-insulin-ratio,
    wherein determining the estimated meal bolus insulin administration rate is based on the estimated meal bolus, a delivery time duration, and a configurable constant.

17. The system of claim 11, wherein the operations further comprise:
    dividing a total meal time into meal time sub-intervals, a first meal time sub-interval starting with a pre-meal glucose measurement before receiving the number of estimated grams of carbohydrates; and
    determining a sub-interval total insulin administration rate for each meal time sub-interval in succession.

18. The system of claim 17, wherein the operations further comprise:
    receiving a number of actual grams of carbohydrates for the meal during a subsequent meal time sub-interval after the first meal time sub-interval;
    determining an actual meal bolus based on the number of actual grams of carbohydrates;
    determining an estimated delivered meal bolus insulin administration rate by multiplying the estimated meal bolus insulin administration rate by an elapsed delivery time duration;
    determining a remaining meal bolus in units of insulin by subtracting a product of the estimated delivered meal bolus insulin administration rate and an actual delivery time period from the actual meal bolus;

determining a revised meal bolus insulin administration rate as the remaining meal bolus divided by a remaining time period duration remaining in the total meal time; and determining a revised total insulin administration rate as a sum of an intravenous insulin infusion rate and the revised meal bolus insulin administration rate.

19. The system of claim 18, wherein the operations further comprise transmitting the revised total insulin administration rate to the insulin administration device, the revised total insulin administration rate when received by the insulin administration device, causing the insulin administration device to administer insulin to the patient the revised total insulin administration rate.

20. The system of claim 11, wherein the operations further comprise displaying, in a graphical user interface displayed on a screen in communication with the data processing hardware, the total insulin administration rate.

\* \* \* \* \*